(12) United States Patent
DiRienzo

(10) Patent No.: US 8,676,609 B2
(45) Date of Patent: *Mar. 18, 2014

(54) ATTACHMENT INTEGRATED CLAIMS SYSTEMS AND OPERATING METHODS THEREFOR

(75) Inventor: Andrew L DiRienzo, Elizaville, NY (US)

(73) Assignee: Integrated Claims Systens, LLC, Elizaville, NY (US)

( * ) Notice: Subject to any disclaimer, the term of this patent is extended or adjusted under 35 U.S.C. 154(b) by 1931 days.

This patent is subject to a terminal disclaimer.

(21) Appl. No.: 11/653,104

(22) Filed: Jan. 12, 2007

(65) Prior Publication Data

US 2007/0260493 A1 Nov. 8, 2007

Related U.S. Application Data

(63) Continuation of application No. 10/196,122, filed on Jul. 17, 2002, now Pat. No. 7,178,020, which is a continuation of application No. 10/036,432, filed on Jan. 7, 2002, now Pat. No. 6,480,956, which is a continuation of application No. 09/592,256, filed on Jun. 12, 2000, now Pat. No. 6,338,093, which is a continuation of application No. 09/232,805, filed on Jan. 19, 1999, now Pat. No. 6,076,066, which is a continuation of application No. 08/824,010, filed on Mar. 25, 1997, now Pat. No. 6,003,007, application No. 11/653,104, which is a continuation of application No. 09/961,308, filed on Sep. 25, 2001, now Pat. No. 7,409,632, which is a continuation of application No. 09/745,489, filed on Dec. 26, 2000, now Pat. No. 6,343,310, which is a continuation of application No. 08/823,977, filed on Mar. 25, 1997, now abandoned, and a continuation of application No. 08/823,978, filed on Mar. 25, 1997, now abandoned, and a continuation of application No. 09/587,284, filed on Jun. 5, 2000, now Pat. No. 6,199,115, which is a continuation of application No. 09/232,805, filed on Jan. 19, 1999, now Pat. No. 6,076,066, which is a continuation of application No. 08/824,010, filed on Mar. 25, 1997, now Pat. No. 6,003,007.

(60) Provisional application No. 60/014,427, filed on Mar. 28, 1996.

(51) Int. Cl.
*G06Q 40/00* (2012.01)

(52) U.S. Cl.
USPC .................................................. 705/4; 705/2

(58) Field of Classification Search
USPC ...................................................... 705/35–38
See application file for complete search history.

(56) References Cited

U.S. PATENT DOCUMENTS

| | | |
|---|---|---|
| 4,264,808 A | 4/1981 | Owens et al. |
| 4,489,379 A | 12/1984 | Lanier et al. |

(Continued)

OTHER PUBLICATIONS

Classified Ad 2—No Title,Chicago Daily Tribune (1872-1922); Aug. 9, 1903; ProQuest Historical Newspapers: Chicago Tribune (1849-1990) p. 21.*

(Continued)

*Primary Examiner* — Hani M Kazimi
*Assistant Examiner* — Clement B Graham
(74) *Attorney, Agent, or Firm* — Leffert Jay & Polglaze, P.A.

(57) ABSTRACT

Systems and methods for processing textual messages which are integrated with one or more digital attachments is described. These systems and methods are useful in the electronic filing and processing of, for example, image data, and of textual data associated with the image data. One particular application of these systems and methods would be for the electronic filing and processing of dental x-rays with patient claim forms.

100 Claims, 10 Drawing Sheets

(56) References Cited

U.S. PATENT DOCUMENTS

| | | | |
|---|---|---|---|
| 4,491,725 | A | 1/1985 | Pritchard |
| 4,500,750 | A | 2/1985 | Elander et al. |
| 4,553,206 | A | 11/1985 | Smutek et al. |
| 4,578,530 | A | 3/1986 | Zeidler |
| 4,680,803 | A | 7/1987 | Dilella |
| 4,831,526 | A | 5/1989 | Luchs et al. |
| 4,912,762 | A | 3/1990 | Lee et al. |
| 4,972,318 | A | 11/1990 | Brown et al. |
| 4,987,538 | A | 1/1991 | Johnson et al. |
| 5,070,452 | A | 12/1991 | Doyle, Jr. et al. |
| 5,148,366 | A | 9/1992 | Buchanan et al. |
| 5,191,522 | A | 3/1993 | Bosco et al. |
| 5,220,501 | A | 6/1993 | Lawlor et al. |
| 5,225,976 | A | 7/1993 | Tawil |
| 5,235,654 | A * | 8/1993 | Anderson et al. ............ 382/180 |
| 5,241,472 | A | 8/1993 | Gur et al. |
| 5,267,155 | A | 11/1993 | Buchanan et al. |
| 5,301,105 | A | 4/1994 | Cummings, Jr. |
| 5,324,077 | A | 6/1994 | Kessler et al. |
| 5,329,447 | A | 7/1994 | Leedom, Jr. |
| 5,359,509 | A | 10/1994 | Little et al. |
| 5,373,550 | A | 12/1994 | Campbell et al. |
| 5,381,457 | A | 1/1995 | Burns |
| 5,416,849 | A | 5/1995 | Huang |
| 5,548,646 | A | 8/1996 | Aziz |
| 5,590,038 | A | 12/1996 | Pitroda |
| 5,657,389 | A | 8/1997 | Houvener |
| 5,664,115 | A | 9/1997 | Fraser |
| 5,736,977 | A | 4/1998 | Hughes |
| 5,754,766 | A | 5/1998 | Shaw et al. |
| 5,764,235 | A | 6/1998 | Hunt et al. |
| 5,829,444 | A | 11/1998 | Ferre et al. |
| 5,832,447 | A * | 11/1998 | Rieker et al. ...................... 705/2 |
| 5,848,198 | A | 12/1998 | Penn |
| 5,930,759 | A * | 7/1999 | Moore et al. ...................... 705/2 |
| 5,930,778 | A | 7/1999 | Geer |
| 5,973,731 | A | 10/1999 | Schwab |
| 6,021,397 | A * | 2/2000 | Jones et al. ................. 705/36 R |
| 6,240,442 | B1 | 5/2001 | Domenikos et al. |
| 2001/0042785 | A1* | 11/2001 | Walker et al. ................. 235/379 |
| 2004/0117302 | A1* | 6/2004 | Weichert et al. ................ 705/40 |

OTHER PUBLICATIONS

Lotus cc: Mail Link to MHS, Release 2 Product Area: Link Products Product Release: Link to MHS 2.0 May 5, 1995.

U.S. Congress, Office of Technology Assessment, Bringing Health Care Online: The Role of Information Technologies, OTA-ITC-624, Ch. 3: Network for Health Information (Washington, DC: U.S. Government Printing Office, Sep. 1995).

Robert A. Cameron and Kenneth G. Carrick, Reengineering DOD Through Enterprise-Wide Migration to Open Systems, Thesis, United States Navy, Naval Postgraduate School, Sep. 1996.

Wayne W. Eckerson, Three-Tier Client/Server Architecture: Achieving Scalability, Performance and Efficiency in Client/Server Applications, Open Information Systems, vol. 10, No. 1, Jan. 1995.

Karen L. Weiss, Integrating Middleware Software Into Open-System Client/Server Systems, Thesis, United States Navy, Naval Postgraduate School, Sep. 1995.

Daniel Minoli, Imaging in Corporate Environments: Technology and Communication, McGraw Hill, 1994.

C.E. Health Corporate Services, A Proposal for a Worker's Compensation System: The Total Solution, Copyright 1993, Publication Unknown.

Finkel, David, The Doctor of the Future, The Washington Post, Nov. 21, 1993.

Maslia, Deborah, Using automation to control receivables: How computers can improve the revenue cycle, Topics in Health Care Financing 20.1 (Fall 1993): 32.

Wilson, Larry, Computer, microfilm link speeds claim handling, National Underwriter, Life, health/financial services ed. 98.40 (Oct. 3, 1994):30.

* cited by examiner

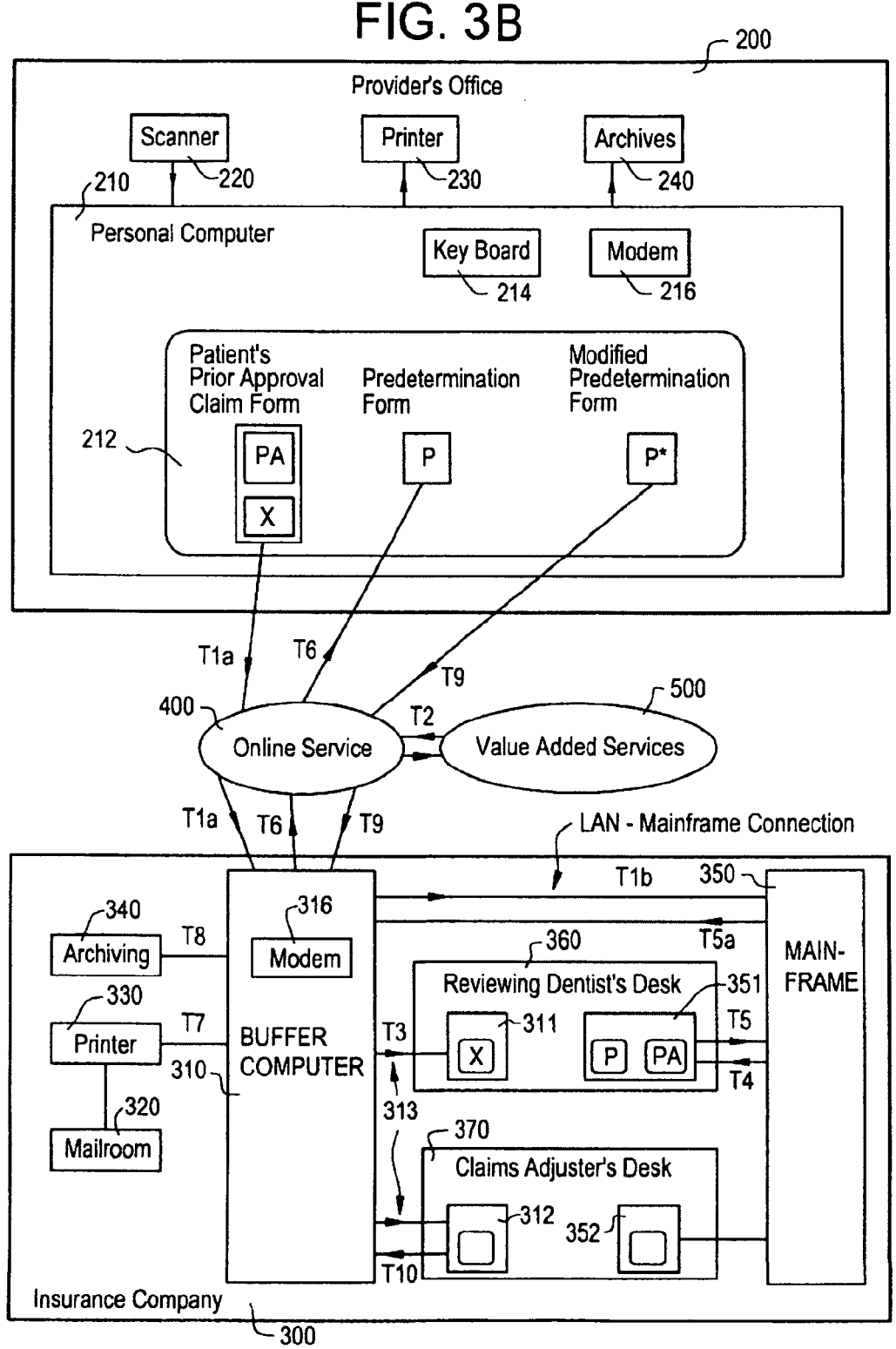

FIG. 5A

DENTAL PRIOR APPROVAL CLAIM (PAC) APPLICATION

Patient X-ray

PIN    PDIN    DIN

| Provider Identification Number | Provider Document Identification Number | Insurance Co. DIN Document Identification Number |
|---|---|---|
| | | |

General Patient Information

Signature:

General Provider Iformation

Signature:

ATTACHMENT INTEGRATED CLAIMS SYSTEMS AND OPERATING METHODS THEREFOR

RELATED APPLICATIONS

This application is a Continuation of U.S. patent application Ser. No. 10/196,122 filed Jul. 17, 2002 now U.S. Pat. No. 7,178,020; which is a Continuation of U.S. patent application Ser. No. 10/036,432 filed Jan. 7, 2002 (now U.S. Pat. No. 6,480,956); which is a Continuation of U.S. patent application Ser. No. 09/592,256 filed Jun. 12, 2000 (now U.S. Pat. No. 6,338,093); which is a Continuation of U.S. patent application Ser. No. 09/232,805 filed Jan. 19, 1999 (now U.S. Pat. No. 6,076,066); which is a Continuation of U.S. patent application Ser. No. 08/824,010 filed Mar. 25, 1997 (now U.S. Pat. No. 6,003,007); which each claims Priority from Provisional Application Ser. No. 60/014,427 filed Mar. 28, 1996. This application is further a Continuation of U.S. patent application Ser. No. 09/961,308 filed Sep. 25, 2001 now U.S. Pat. No. 7,409,632; which is a Continuation of U.S. patent application Ser. No. 09/745,489 filed Dec. 26, 2000 (now U.S. Pat. No. 6,343,310); which is a Continuation of U.S. patent application Ser. No. 08/823,977 filed Mar. 25, 1997 (now abandoned), and U.S. patent application Ser. No. 08/823,978 filed Mar. 25, 1997 (now abandoned), and is further a Continuation of U.S. patent application Ser. No. 09/587,284 filed Jun. 5, 2000 (now U.S. Pat. No. 6,199,115) as a Continuation of U.S. patent application Ser. No. 09/232,805 filed Jan. 19, 1999 (now U.S. Pat. No. 6,076,066) as a Continuation of U.S. patent application Ser. No. 08/824,010 filed Mar. 25, 1997 (now U.S. Pat. No. 6,003,007); which each claims Priority from Provisional Application Ser. No. 60/014,427 filed Mar. 28, 1996. Each of the foregoing applications is commonly assigned and incorporated by reference herein in their entirety.

BACKGROUND OF THE INVENTION

The present invention relates generally to an attachment integrated claims (AIC) system for preparing and processing forms with integrated attachments. More specifically, the present invention relates to an AIC system for preparing and processing digital insurance claims including Prior Approval Claim (PAC) Applications containing both a text form and an integrated digitized attachment. A method of operating a totally digital AIC system is also disclosed.

High administrative costs for filing and processing health insurance claims have been the bane of the health insurance industry from its inception. Over the years, many attempts have been made to develop a faster and more cost effective claims processing system. Three stages in this development effort are described in the following correspondingly numbered paragraphs.

(1) The original system involved hard copy paper claims only, with transmission and all processing done manually. Originally, an insurance claim was filed by the patient or the health care provider filling out a paper form. The completed paper form was then mailed to the insurance company. At the insurance company, the paper claim form went through a series of administrative steps, all the time remaining as a hard copy paper object. When a decision was made, the decision was written up and archived with the claim form; a hard copy was also sent to the patient and/or provider along with the payment.

(2) The first significant advancement resulted from the introduction of the mainframe computer. This allowed for electronic processing within a given insurance company, i.e., once the claim was on the computer inside the company, the paper form could be dispensed with. Computerization is a highly effective way of reducing administrative overhead in claims processing.

Thus, mainframe computers were purchased and installed internally at the insurance companies. Since these computers were intended for internal use only, each company thought only of its own needs and had its claims management software customized. While the claims management software for a number of insurance companies would be written in the same high-level programming language, e.g., COBOL, the similarity between software programs often ended there. There were many virtues to these early systems, primarily with respect to decreased administrative costs, but a major drawback was that the data for each "paper" claim had to be entered into the computer to form an electronic claim. This necessitated the manual transcription of exactly the same information that had been handwritten into the original paper claim before it was sent to the insurance company.

(3) The next advancement was the electronic filing of claim forms. This was made possible by the introduction of the personal computer and modem into the provider's office. The main purpose of this stage was to eliminate the manual re-entry of information into the insurance company mainframe.

The basic idea was to have the providers fill out an electronic claim form, instead of a paper claim form. This electronic form, which would be stored in the memory of their PCs, would then be transmitted, as a computer file, to the insurance company. It could then be integrated directly into the electronic claims processing system without the manual re-entry of data. Thus, the technology existed to produce a system that computerized the overall filing and processing of the insurance claim from the point of entry, the provider's office, to the final report of the claims adjuster.

Although the idea was straightforward, implementation was not. Two basic problems had to be overcome in order to create a viable system. First, the information contained in the electronic claim form had to be integrated into the claims processing software at the insurance company. Second, a majority of providers have to be able to interface with a majority of insurance companies, i.e., insurance company mainframe computers. However, because of the way computers had entered the insurance industry originally (stage #2), there was no industry-wide standard, i.e., the legacy mainframe computers of the different insurance companies were incompatible. This was true both with respect to the type of software used and with respect to the information that each company required on its claim form.

One attempt to deal with these problems was the creation, by a consortium of insurance companies, of the National Electronic Information Corporation (NEIC). NEIC's basic function is that of a clearinghouse. It interfaces between the insurance companies and the service providers. It also establishes rigid standards that must be met in order to transmit an electronic claim form to an insurance company. In practice, the service provider sends an electronic claim to a vendor, who performs a service such as screening of the form. The vendor then transmits the form to NEIC, which then re-transmits it to the patient's insurance company. Since it is a computer file, the information in the electronic claim form can then be entered directly into the company's mainframe claims processing system, without the manual re-entry of data, and then processed.

Thus, a coherent system was created that allows for the electronic filing, transmission, and processing of insurance claims. This system is employed by thousands of providers and hundreds of insurance companies.

NEIC was designed to act as a clearinghouse for claims that are 100% text and that conform to very restrictive formats. For claims that meet these conditions it functions well, resulting in substantial savings on administrative costs for the insurance companies. It has been estimated that going to this third stage system results in savings of as much as 60% in claims processing costs.

But there are many claims that do not meet these conditions. These would include claims that require additional text information that doesn't fit into the prescribed format and/or claims that require non-text information. In general, these are called "claims with attachments." "Attachments" are any additional information that must be sent with the "standard text claim form." This could include: pictures, graphs, additional text not allowed on the standard claim form, sound recordings, etc.

An example of such a claim would be the PAC (Prior Approval Claim), which may be alternately denoted as a "Pretreatment Claim". These are claims that are sent to the insurance carrier before a procedure is performed. For example, pretreatment claims are often required by dental insurance companies on any procedure over a specified amount, e.g., $200. The aspect of this type of claim which renders it incompatible with the present electronic claim processing system is that the insurance companies require that additional medical evidence be included, i.e., attached to, the text part of the claim form. In an exemplary case, the additional medical evidence is an x-ray.

The goal of the insurance company is to review the claim, i.e., both the text form and attachment, and to do so in a cost effective manner. The natural next stage in the development of claims processing systems is to attempt to computerized this process.

Scanners are now available that can digitize a dental x-ray, i.e., convert it into a computer file that can be viewed on a monitor. But transforming the medical evidence into digital form is not enough to facilitate electronic processing of claims with attachments. One must also take into consideration the existing claims processing infrastructure, i.e., the legacy infrastructure.

The difficulty with trying to include a digitized x-ray for processing with an electronic claim form, within the current infrastructure, is multifaceted. First, NEIC does not at the present time allow this type of information to be transmitted through NEIC to the insurance companies. Second, with the current system, the claims adjusters access claims information through terminals connected to mainframes. But there is the inherent problem of displaying images on mainframe computers. This is especially true of mainframe computers running software written in business programming languages such as COBOL. It might be thought that a solution to this problem would be to replace the terminal with a PC. Although many personal computers provide the graphics support needed to display the digitized x-ray, there are significant problems in interfacing a PC with a mainframe computer. For example, in order to interface with the mainframe computer, PCs often run terminal emulation software which permits the PC to act like a dedicated, dumb terminal attached to the mainframe computer. Terminal emulation software is notoriously lacking in graphics capability. And finally, getting a digitized x-ray from one provider to one insurance company is not all that is needed. Rather, what is really needed is an industry-wide system whereby a provider can interact with any insurance company. This results in a massive interfacing problem since there are multitudes of insurance companies using different legacy hardware systems and company unique software.

Each time a way has been found to more fully utilize computers in claims processing systems, the administrative costs associated with claims processing have gone down. However, in the area of "claims with attachments," no coherent industry-wide system exists that allows for the integrated filing, transmitting and processing of these claims electronically, i.e., via computers. Thus, when attachments are required, providers are forced to submit hard copy claim applications, while insurance companies labor under an administrative system that is a hybrid between a manual and an electronic system, i.e., a hybrid between stage #1 and stage #2. This hybrid system, which is described in greater detail below, is labor intensive, prone to problems, and slow. For providers, insurance companies, and patients, this is a time-consuming, costly and irritating process.

In short, there is at least one type of insurance claim that has not, until now, been able to avail itself of the third stage of computerization, as described above. In fact, there are even difficulties with the second stage. This group includes any claim whose "standard text form" must be accompanied by additional information that does not fit into this standard format, e.g., x-rays, EKGs, additional text information such as Operating Room Reports, etc. In general, these are referred to as "attachments." One primary example of this would be Prior Approvals for dental procedures. Prior Approval Claim (PAC) applications are those claims that are submitted for the purpose of receiving a predetermination of benefits from the insurance company for a procedure that hasn't as yet been performed.

In the area of Prior Approval Claims, the goals of the insurance companies are to validate the necessity of the procedure and to determine whether the patient's insurance policy obligates the insurance company to pay for such a procedure. This requires that the insurance company itself review the medical evidence. For an insurance company's in-house dentist, for example, to make this appraisal, the dentist is required to review both the "text form" and the accompanying x-ray of the patient. However, the presence of a film x-ray means that electronic claims methods cannot be implemented. The savings associated with electronic claim processing is not available with respect to Prior Approval Claim forms.

Nationwide, there are approximately 200,000 dental PACs filed per week. Roughly, for every PAC application there will be eventually a Final Payment Claim (FPC) submitted when the medical procedure is completed. It is estimated that the overall administrative cost is $25 per PAC form and $10 for the Final Payment Claim. It is also estimated that if a coherent electronic system could be implemented, it would reduce these administrative costs to $15 per PAC and $5 per Final Payment Claim. The savings could amount to as much as $3,000,000 per week collectively for the health care industry for dental PACs and FPCs alone.

An example of a hybrid system of claim processing currently in use will now be described with reference to FIGS. 1, 2A and 2B.

Referring first to FIG. 1, the U.S. Postal Service, denoted as 100, connects the service provider's office 200 with the insurance company 300. It will be appreciated that, since PAC form handling is entirely manual at location 200, the service provider's office is depicted as lacking computer equipment. In contrast, the insurance company typically has at least one mainframe computer 350 to which terminals 351, 352 on the respective reviewing dentist's desk 360 and claims adjuster's desk 370 are connected. It should also be noted that the mail room 320 is charged with a variety of tasks associated with the incoming and outgoing correspondence, as discussed in greater detail below.

As will be appreciated from FIG. 1, a paper PAC form is filled out by the patient and/or the provider and, along with the substantiating x-ray, is mailed to the patient's insurance company. Upon entering the mail room of the insurance company, the PAC form is assigned a document identification number (DIN) and the data from the PAC form is then entered into the company's mainframe computer. This same DIN is affixed to the x-ray. The x-ray is then manually delivered to the reviewing dentist.

By using the DIN on the x-ray, the reviewing dentist downloads, from the mainframe computer, the textual part of the patient's PAC application. The dentist makes a decision, records it in the memory of the mainframe computer, and has a hard copy of the Predetermination form posted back to the provider. Once the procedure has been completed, the provider's office completes the Predetermination form, or fills out a separate Final Payment Claim (FPC) form. This is then posted to the insurance company. A chronological, detailed, step-by-step description of the hybrid system will now be provided with reference to FIGS. 1, 2A and 2B.

During step S1, the dentist decides that a costly procedure is necessary for a patient whose insurance carrier requires prior approval for such treatment. During step S2, the dentist provides the patient with his diagnosis and gives the patient an estimate for performing the recommended procedure. The dentist then asks the patient to contact his insurance carrier, or plan administrator at work, to obtain the necessary PAC form. During step S3, the patient completes that portion of the PAC form that pertains to him, signs the form, and sends it to his provider.

After the PAC form arrives at the provider's office at step S4, one of the office personnel retrieves the patient's file and the PAC form at step S5, extracts the patient's x-ray, either the original, a copy of the original, or a second, previously taken x-ray, during step S6, and the PAC form is filled out entirely by hand, i.e., the information about the provider has to be entered every time a new PAC form is received, during step S7. Copies of the completed form are made and are placed in the patient's file during step S8. The envelope containing the PAC form is addressed to the appropriate insurance company at step S9. The form and the x-rays are placed in the envelope during step S10. An entry is made in both the patient's computer file (if the provider's office is equipped with one) and his hard copy file indicating that the PAC form has been sent during step S11 and, finally, during step S12, the envelope is mailed. See task T1 in FIG. 1.

The envelope meanders through the U.S. Postal Service 100 for several days at step S13 until the envelope finally arrives at the mail room 320 of the insurance company 300 at step S14. In the mail room, the envelope is opened (step S15), the data from the PAC form is entered into the insurance company's mainframe computer 350 and is given a Document Identification Number (DIN) that identifies the patient and the current claim application (step S16). See task T2 in FIG. 1. During step S17, the x-ray is labeled with the same DIN. It will be appreciated that the DIN on the x-ray and in the document now on the mainframe computer must be identical. It will also be appreciated that for some insurance companies, this manual processing is contracted to an outside agency, which would require several more steps, which steps will not be described further.

During step S18, the x-ray is manually forwarded to the reviewing dentist's area. See task T3 in FIG. 1. During step S19, the PAC form is transferred to a directory and waits to be read by a reviewing dentist.

During step S20, a group of x-rays arrives from the mail room at the reviewing dentist's area. A film x-ray is pulled out of the waiting pile by the dentist during step S21 and the reviewing dentist then accesses the "PAC form" directory during step S22 by, for example, reading the DIN from the x-ray and typing the DIN into the computer. The electronic PAC form corresponding to this x-ray is located in memory and downloaded to the reviewing dentist's monitor during step S23.

The procedure requested is read off the terminal monitor and the film x-ray is reviewed during step S24 and a determination is made during step S25. It will be appreciated that a determination refers to either an approval or a denial of the request. Assuming that the procedure is approved, a statement (or explanation) of benefits (EOB) is also generated. For the purposes of this discussion, it will be assumed that the procedure is approved; a denial would necessitate a parallel but alternative set of processing steps, which steps will not be further described. During step S26, the insurance company's Predetermination form is filled out either electronically or by hand. For an electronic Predetermination form, the form is saved to the memory of the insurance company's mainframe computer during step S27. The x-ray is returned to the mail room during step S28. See task T4 in FIG. 1.

Following approval, a paper copy of the Predetermination form is made during step S29. See task T5 in FIG. 1. An envelope is then addressed to the referring dentist and the Predetermination form is placed in the envelope during step S30. During step S31, the corresponding x-ray is matched with the Predetermination form and, during step S32, the corresponding x-rays are placed in the envelope. The envelope then goes back into the U.S. Postal System 100 during step S33. See task T6 in FIG. 1.

Some days later, the envelope finally arrives at the dentist's office 200 and is opened during step S34. The results are noted in both the patient's paper file and computer file during step S35, the x-rays are returned to the patient's paper file at step S36, and the patient is notified of the approval and a date is set for performing the approved treatment during step S37.

The treatment is completed during step S38 and the Final Payment Claim (FPC) form is filled out during step S39. It will be appreciated that the Final Payment Claim form, for many insurance companies, is merely a subsection of the Predetermination form generated in step S29 (See the paper denoted P* in FIG. 1.); alternatively, the Final Payment Claim form could be yet another form supplied by the insurance company.

The Final Payment Claim form is then sent back to the insurance company with a copy of the signed Predetermination form during step S40. See task T7 in FIG. 1. The Final Payment Claim form enters the mail room as a paper form and the final processing begins during step S41. It will be appreciated that the processing of the Final Claim Form typically requires making several entries in the information stored on the mainframe computer 350 and may require the preparation of one or more forms needed to authorize payment of the final claim. However, since an attachment is not normally associated with the Final Claim Form, additional discussion regarding disposition of the Final Claim Form within the insurance company will not be provided.

Thus, the hybrid system under discussion is one that starts in the provider's office when a patient is told that a PAC form is needed and continues until the procedure has been completed and a Final Payment Claim form has been submitted to the insurance company for payment. It will be appreciated that a myriad of problems and inefficiencies arise due to claim processing in accordance with the hybrid system. The principal problems are as follows:

1. All information needed to complete the PAC form has to be entered by hand. Moreover, all of the information on the PAC form is also manually transcribed in order to transfer the information from paper to the insurance company's mainframe computer. Both of these manual data entry process steps are time consuming, very costly, and prone to human error;
2. The x-ray film and the text form are put together and then separated several times during the overall claim processing;
3. The hybrid system requires that a hard copy of the x-ray be sent to the insurance company. Generally, this x-ray is returned to the provider. Moreover, the requirement that the dentist provide the x-ray typically means that a duplicate x-ray has to be made by the dentist, which increases the dentist's cost for the service. Oftentimes, the duplicate x-ray is of poor quality and cannot be read;
4. Because prior approval claim forms cannot be processed electronically, and because PAC forms make up half of all the claims that approximately 20,000 oral surgeons, periodontists, and orthodontists make each year, these 20,000 providers have no compelling reason to initiate electronic claims for Final Payment Claims;
5. The document identification number is affixed to the x-ray and the electronic text in two different processes, one physical and the other electronic. This leads to errors;
6. After the procedure has been completed, almost identical information may again have to be entered by hand in order to prepare the Final Payment Claim form;
7. While direct digital x-ray equipment is available, it is difficult to integrate a digital x-ray into the current hybrid claims processing system, i.e., these computerized images would first have to be transferred to film, which would, of course, negate the major advantage for using direct digital x-rays;
8. Some insurance companies would like to require that x-rays accompany all dental claims; they are prevented from doing so because of the high administrative overhead associated with handling hardcopy claims;
9. The patient has to obtain the PAC form from the insurance company or his employer. In either case, this causes the patient time, is an irritant, and imposes unnecessary delays on the delivery of medical care to the insured;
10. With the hybrid system, no prescreening of the PAC form for errors is performed before the PAC form goes to the insurance company; and
11. Provider information, i.e., the dentist's information, often has to be entered separately on each new PAC form that is submitted.

In summary, the current method for handling PAC applications is a hybrid system somewhere between a Stage 1, a totally paper-based manual processing system, and a Stage 2 internally computerized insurance company processing system. It is part electronic and part hard copy. Also, each form must be handled twice, once as a hard copy and once as an electronic copy. This is the source of a great many of the above described problems. Moreover, the current hybrid method is costly. The process starting at the provider's office, continuing through the insurance company and finally to the return of the Predetermination form to the provider has been estimated to cost $25. Furthermore, the whole process is filled with potential for error, frustration, wasted time and money.

The workflow for the filing and processing of a PAC form was described above with respect to the dental health insurance which was used, by way of example, to illustrate the circuitous process involved when a hard copy attachment is present. Other types of claims, or attachments, or different insurance companies might require slightly different steps. For example, instead of returning an attachment, as describe above, the attachment might need to be microfilmed and archived, or some of the information contained in the attachment itself might need to be entered into the mainframe. Regardless of these differences, there are similarities in the problems that arise in processing such claims.

The present invention was motivated by the desire to overcome the problems associated with the above-described hybrid system for processing "forms with attachments." The intent was to create a coherent system that allows for the electronic filing, transmission, and processing of these forms, e.g., claims. That is, a system that would create a Stage #3 level of computerization for "forms with attachments." More specifically, the present invention was motivated by the desire to eliminate, to the maximum extent possible, all processing steps described above which are in any way connected with the presence of a hard copy attachment.

SUMMARY OF THE INVENTION

One purpose of the present invention is to create a coherent system that allows for the electronic filing, transmission, and processing of "insurance claims with attachments," and to thereby overcome the many deficiencies of the hybrid system claims processing methodology described above.

Thus, one object according to the present invention is to provide a PAC form processing system which minimizes the necessity of manual data entry. According to one aspect of the present invention, only about 40% of the information needed to complete the PAC form has to be entered by hand. According to another aspect of the present invention, the amount of information that has to be manually re-entered by an operator is essentially zero.

Another object according to the present invention is to provide a PAC application processing system which eliminates handling errors resulting in a mismatch between, for example, a PAC form and an associated patient x-ray. According to another aspect of the invention, mismatch errors are virtually eliminated since the electronic x-ray and the associated text are never separated; field data included in, for example, the PAC form is copied and transferred between the server and the mainframe computer systems inside the insurance company. According to yet another aspect of the invention, mismatch errors are virtually eliminated since no hard copy of the x-ray is ever sent to the insurance carrier.

Still another object according to the present invention is to provide a PAC application processing system which increases the number of service providers employing electronic claims systems to thereby reduce the overall claims processing costs. Since a PAC form can now be handled electronically in accordance with the present invention, electronic final payment claims become viable for approximately 20,000 additional dentists.

A still further object according to the present invention is to provide a PAC application processing system in which Document Identification Numbers, or some other method of uniquely specifying the PAC, are simultaneously associated with both the text and the x-ray by a single computer entry.

Yet another object according to the present invention is to provide a PAC application processing system which operates at lower cost. Cost efficiencies are readily achieved according to the present invention by eliminating the need to send a physical x-ray with the claim.

Another object according to the present invention is to provide a cost effective claim processing system wherein little or no information on either the PAC form or the Predetermination form has to be manually re-entered.

Still another object according to the present invention is to provide a system for packaging textual data with an associated digitized x-ray for transmission to an insurance company. It will be appreciated that direct digital images are easy to integrate into the system because such images are already in the form of a computer file.

Another object according to the present invention is to provide a totally digital PAC application processing system which can accommodate both text and digitized x-rays at low cost, thereby allowing insurance companies to require x-rays with all claims because such requirements will not significantly increase the processing cost associated with non-x-ray documented claims.

An additional object according to the present invention is to provide a totally digital PAC application processing system in which a customizable claim form, i.e., the PAC form, which addresses the needs of all insurance carriers is stored in the memory of the computer in every service provider's office. This, in combination with a non-clearinghouse communications channel and having AIC system software at all of the insurance carriers, then eliminates the need for imposing industry-wide standards, such as ANSi ASC X12, for claim-related electronic transactions. The present invention allows each individual insurance company to get the information that it requires and to get that information in what ever format that insurance company prefers. Moreover, the ability to transmit the customizable claim form and integrated attachment to an insurance carrier via a non-clearing house communications channel advantageously permits the transmission of other types of claims, including worker's compensation claims, to the insurance carrier. In addition, it will eliminate the irritant of the patient or provider having to obtain a PAC form from a particular insurance company.

Another object according to the present invention is to provide a totally digital PAC application processing system in which prescreening of information entered into a PAC form, which is stored in the memory of the computer in the service provider's office, is easily performed.

Yet another object according to the present invention is to provide a totally digital PAC application processing system in which provider information is automatically entered into each PAC form.

These and other objects, features and advantages of the invention are disclosed in or will be apparent from the following description of preferred embodiments.

BRIEF DESCRIPTION OF THE DRAWINGS

The preferred embodiments are described with reference to the drawings in which like elements are denoted by like or similar numbers and in which:

FIGS. 3A-3C are a combination high level block diagrams and flow diagrams which are useful in understanding the operation and system of Prior Approval Claim form processing according to various embodiments of the present invention;

FIGS. 5A and 5B illustrate alternative embodiments of the attachment integrated claim application according to two of the preferred embodiments of the present invention.

DETAILED DESCRIPTION OF THE PREFERRED EMBODIMENTS

Figure 1:
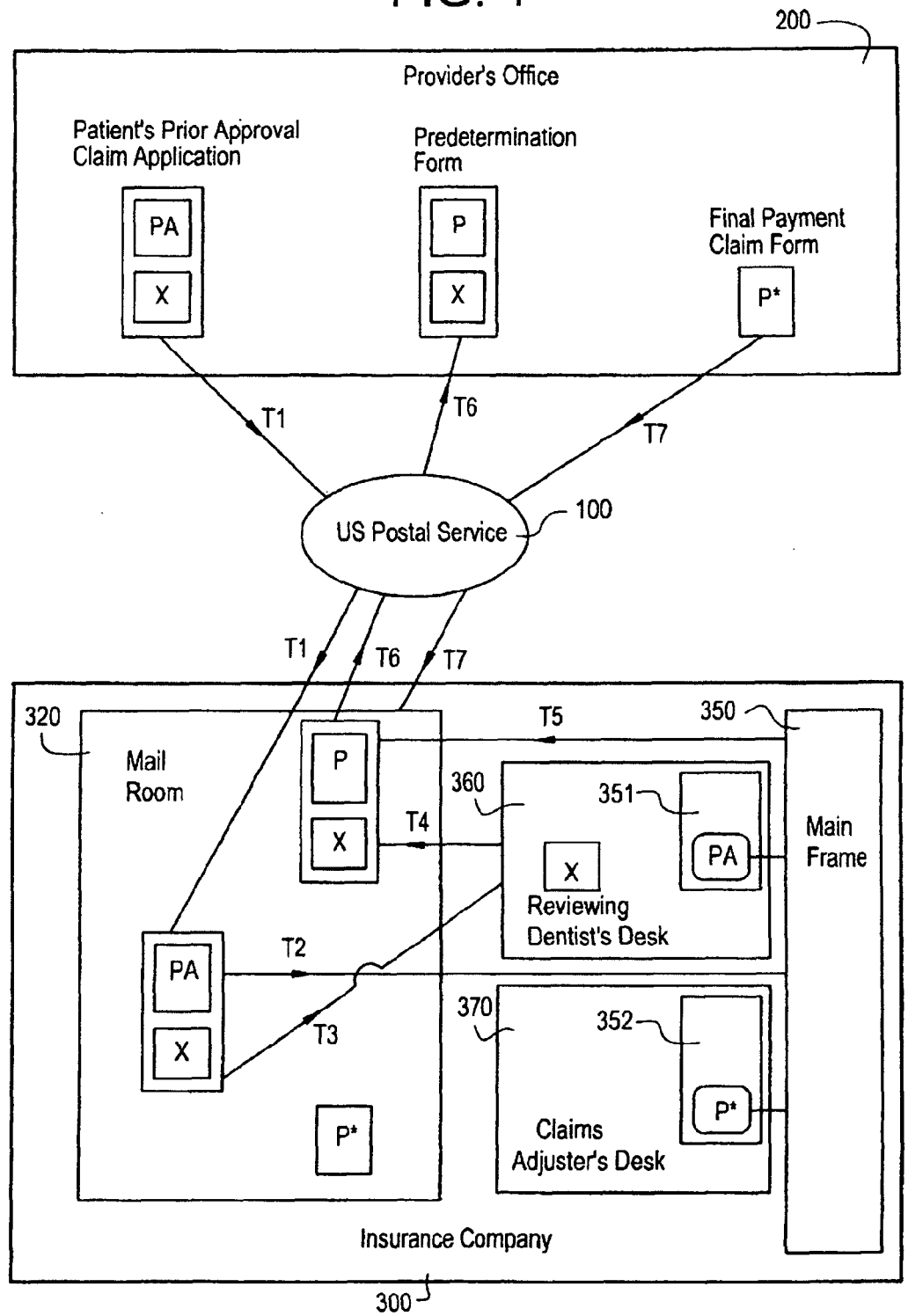
FIG. 1 is a combination high level block diagram and flow diagram which is useful in understanding the operation and attendant problems of the current hybrid system for Prior Approval Claim form processing.
Figure 2A:
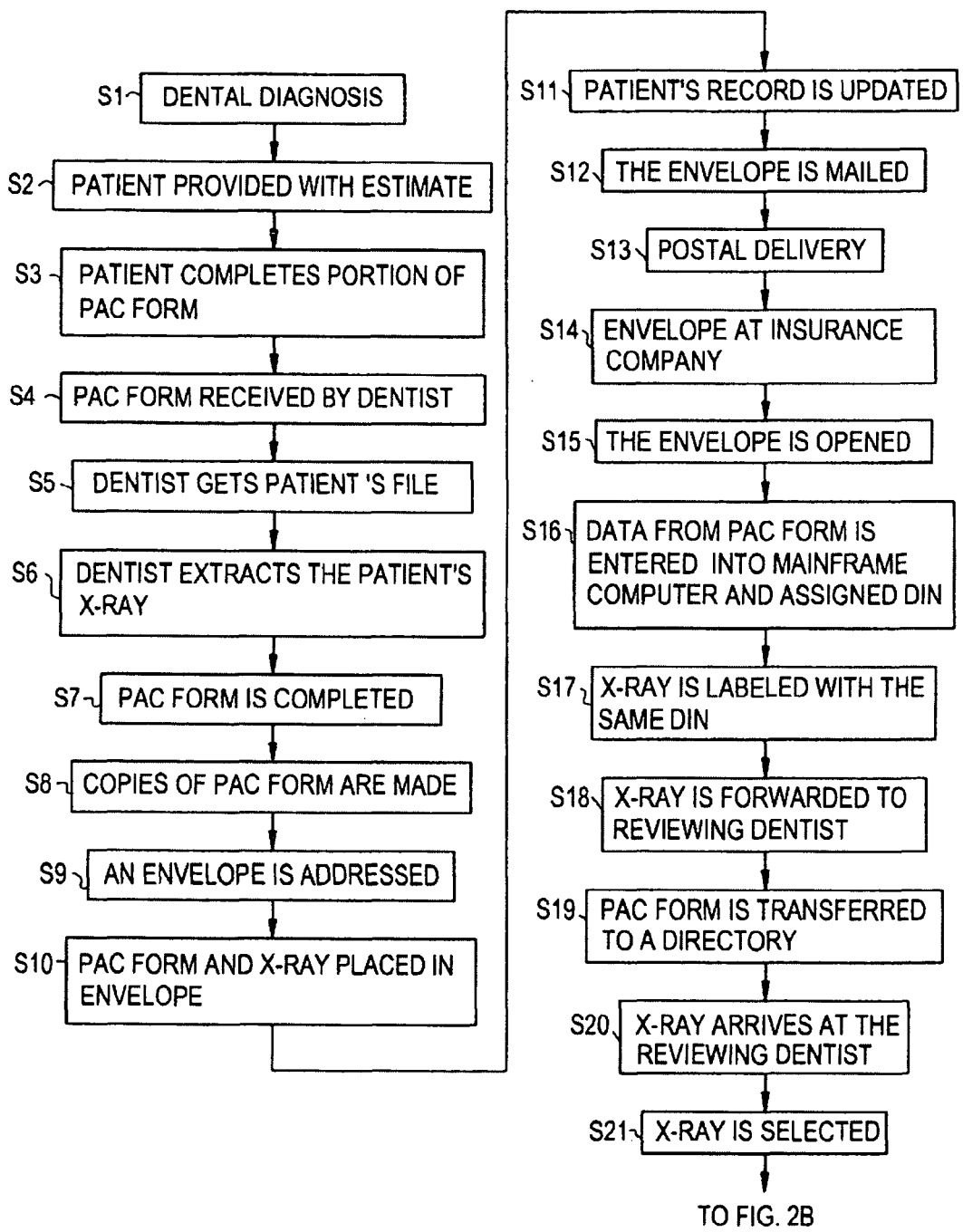
FIGS. 2A and 2B collectively form a flow chart which illustrates in greater detail the steps needed to implement the hybrid system of FIG. 1.
Figure 2B:
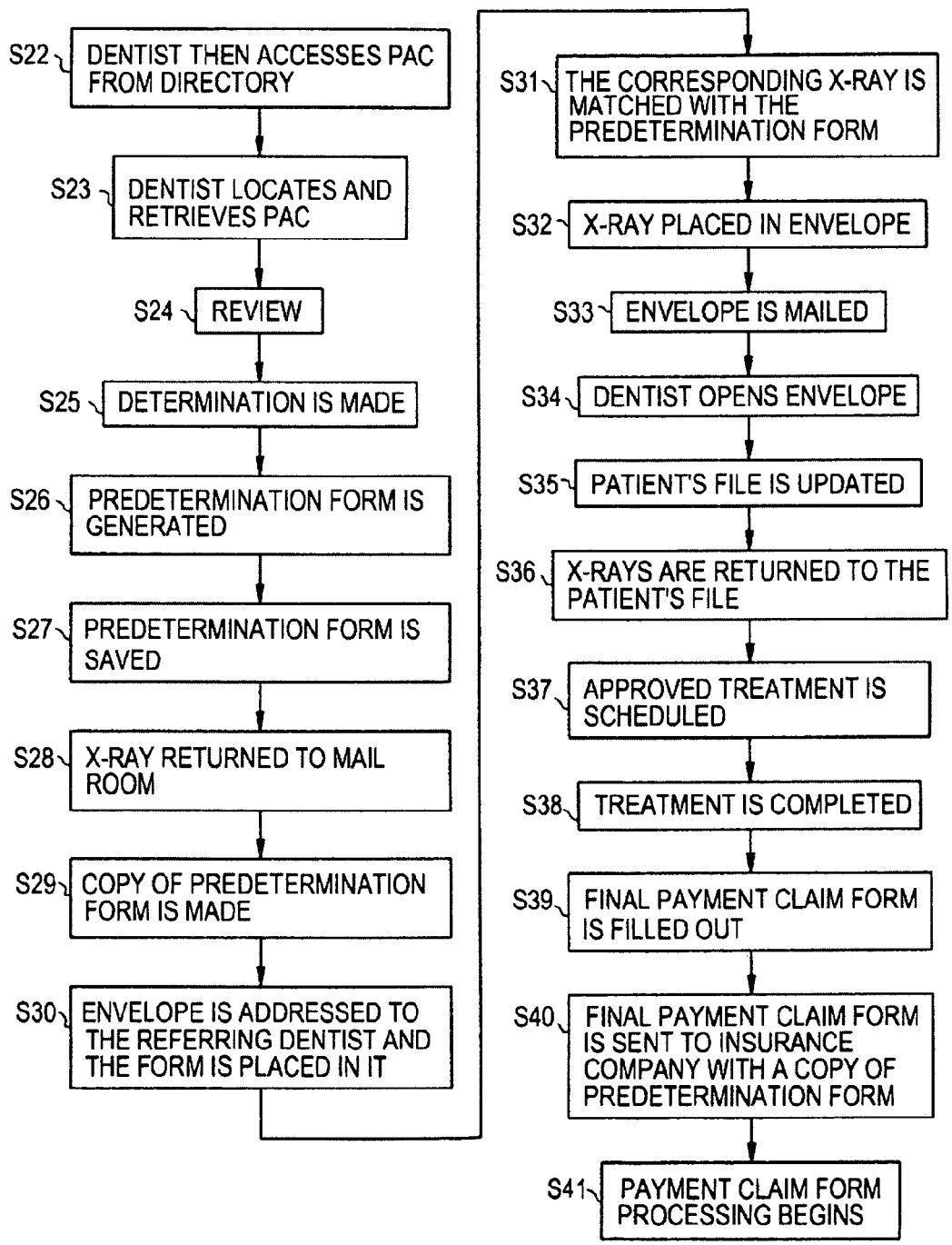

The present invention is a system and corresponding method implemented by software loaded onto the system for processing textual messages which are integrated with one or more attachments. Heretofore, such attachments could not be readily and/or usefully incorporated with the textual message. Hereinafter, the term Attachment Integrated Claim (AIC) Application will be used to denote a claim application including a text portion and a digital attachment portion. An exemplary embodiment of the present invention combines a patient's digitized x-rays with an electronic insurance claim form to create an electronic Prior Approval Claim (PAC) Application. Another preferred embodiment of the present invention is an industry-wide system for the electronic filing and processing of these PAC Applications.

It should be noted that the term "digital attachment" as used hereinafter is not limited to a digitized image or x-ray. The term "digital attachment" is understood to embrace x-rays, CTs, MRIs, EKG or EEG recordings, i.e., strip charts, digitized video signals such as Moving Picture Experts Group (MPEG) compressed video signals, transcriptions of Operating Room Notes, estimates for repairs to a house or car, Explanation of Benefits (EOBs), additional ASCII text, and the like. Moreover, all particulars regarding a specific "attachment," such as medical specialty, acquiring modality, the patient's problem, etc., are to be ignored, since such details have absolutely no bearing on the various embodiments of the present invention. The only requirements regarding digital attachments are that the information must be something that can be digitized, i.e., put into the form of a computer file, and that once in this form, it can be "read, reviewed or interpreted" by the person or organization receiving it.

The preferred embodiments according to the present invention will be described with reference to FIGS. 3A-3C and FIG. 4. It should be mentioned that the descriptions that follow describe the embodiments of the invention as they are used in connection with dental insurance forms. However, the present invention is not limited to systems for the processing of dental insurance claims. Rather, the present invention encompasses the preparation, transmission and processing of data packages including a plurality of data fields wherein at least one of the data fields is a digital attachment, e.g., a digital or graphic image. For example, casualty insurance claims with supporting documentation, i.e., pictures taken with a digital camera, are within the scope of the present invention.

Before presenting a detailed description of preferred embodiments according to the present invention, a brief overview of the operating method steps associated with formation, transmission and processing of the PAC Application will now be presented. In an exemplary and non-limiting case, the essential steps of the operating method include a first subroutine for completing and transmitting needed information to a designated insurance company. This subroutine includes steps for:

(1) Retrieving an appropriate electronic PAC form from storage in the computer's memory and displaying the PAC form on the computer screen;
(2) Filling out of PAC form on the computer screen;
(3) Digitizing, e.g., scanning, the patient's x-ray;
(4) Combining the digitized x-ray and the electronic PAC form into the patient's PAC application; and
(5) Transmitting the patient's PAC application to the designated insurance company.

After the PAC application is received by the insurance company, the insurance company performs another subroutine, which includes steps for:

(6) Reviewing the PAC application;
(7) Generating an electronic Predetermination form when the application has been reviewed; and
(8) Transmitting the electronic Predetermination form back to the insured's Service Provider.

When the electronic Predetermination form from the insurance company is received by the service provider, an additional subroutine is performed by the service provider. This subroutine advantageously includes steps for:

(9) Reading the electronic Predetermination form;
(10) When the approved procedure has been performed, adding completion data to the electronic Predetermination form; and
(11) Transmitting the annotated electronic Predetermination form back to the Insurance Company.

When the annotated electronic Predetermination form is received from the service provider, the insurance company performs a final subroutine, which includes steps for:

(12) Reviewing the annotated information; and
(13) Issuing the final payment to the service provider.

Figure 3A:
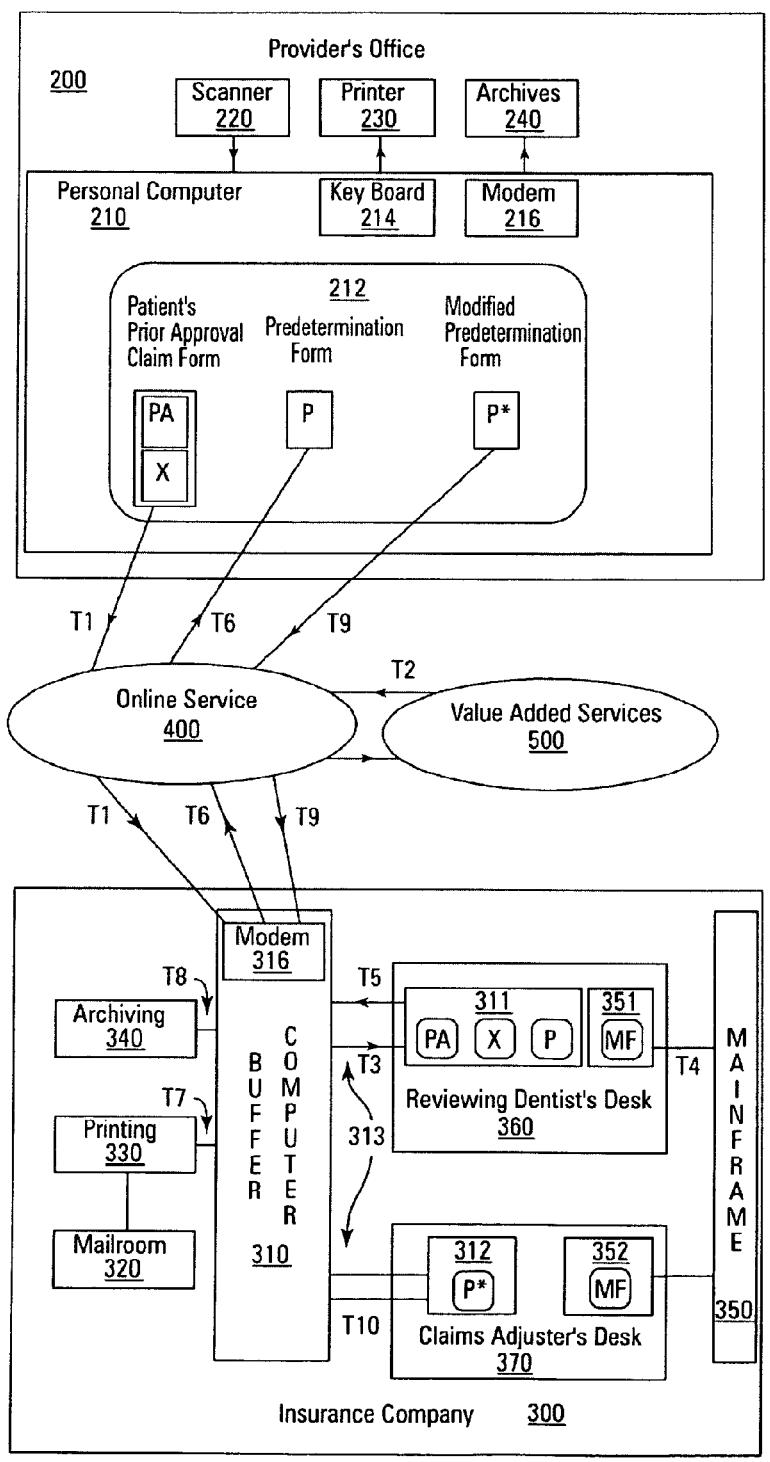

Embodiment of FIG. 3A

For the embodiment as shown in FIG. 3A, the overall system according to the present invention includes the computer components 200 located in the health care provider's office and the computer components 300 located on the premises of the insurance company. Infrastructure 400, which advantageously may be an existing on-line service company, is preferably used in one embodiment of the present invention to facilitate communication between the components 200 in the service provider's office and the components 300 at the insurance company. Preferably, components 500, which are located at a value-added service company, permit services ordered by the service provider, patient, or insurance company to be performed. It should be noted that the components 500 may duplicate a subset of the components 300 found at the insurance company and, for that reason, description of the components 300 alone will be provided below.

As shown in FIG. 3A, the components 200 include a personal computer 210 including a screen 212, a keyboard 214 and a modem 216, connected to a scanner 220, a printer 230 and an archiving device 240, e.g., a large memory for storage of digital information. Device 240 advantageously may be a writeable compact disc read only memory (CD-ROM), i.e., a so-called write once-read many (WORM) device, a hard disk drive, a tape back up device or a removable hard disk device. It should be recognized that the computer 210 advantageously can be a computer system including a central processing unit, a graphic display processor, the graphic display device 212, and several memories including both solid state memories and a hard disk drive. It should also be noted that the archive device 240 and one of the memories associated with computer 210 may be the same memory device.

Components 300 located at the insurance company include the previously described mainframe or legacy computer 350 and terminals 351, 352. In addition, a buffer computer 310, which may be a network server, includes a modem 316 and is connected to a printer 330 and a storage device 340. The printer 320 may provide copies of documents directly to the mailroom 320. Preferably, the computer 310 is connected to personal computers or work station terminals 311, 312 via a local area network (LAN) 313.

The method for operating the system according to the embodiment of the present invention as depicted in FIG. 3A will now be described in detail.

The method starts at step S101 with the service provider's diagnosis that a costly procedure is necessary. It is then determined that the patient needs prior approval from his insurance company. During step S102, the patient is provided with an explanation of the procedure and a cost estimate for that procedure. The service provider and the patient then prepare the needed PAC Application.

During step S103, a member of the service provider's office staff accesses the Attachment Integrated Claims (AIC) software stored in non-volatile memory on the service provider's computer system 210, which software advantageously is Graphic User Interface (GUI) software. Preferably, this AIC software is written in C++, Visual Basic, JAVA or some other appropriate graphical programming language.

It will be appreciated that commercial software packages, such as LOTUS NOTES™, have been designed with the capability of addressing combinations of text and graphics files. However, the purpose of these packages is to create an "environment" or "platform" in which specific applications can be developed. In contrast, the preferred embodiments according to the present invention are directed at providing integrated text and graphics files within a coherent system and methodology for addressing the specific needs of the work flow, preferably of a particular industry. That is, it is a particular application. It is possible, but not necessary, that the software needed to implement the preferred embodiments of the present invention can be developed within the frame work of the environment created by something such as LOTUS NOTES™.

Contained within the AIC software are PAC forms for insurance companies using the AIC system. When one of these is opened it acts as a template upon which a new computer file will be based. This computer file will ultimately contain the patient's PAC Application.

Figure 5B:
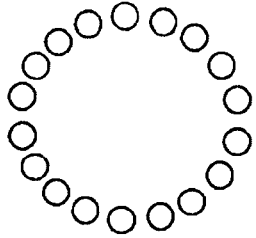

It will be appreciated that the PAC form when displayed on the computer's screen 212 contains boxes, such as those depicted in FIGS. 5A and 5B, in which alpha-numeric characters can be entered so that, when the characters are entered in these boxes they are entered so as to fill a "field," a delimited alpha-numeric character string. Being a "field," the information denoted by the characters can be transferred to and used in completing other fields in related documents. Also, the information itself, or lack thereof, can be used as a logic control device, e.g., used to remind the preparer that critical information has not been entered.

In an exemplary case, the PAC forms of many insurance companies have been encoded and stored in memory on the service provider's computer system 210. This can be advantageously done in the following way. The PAC forms for all the insurance companies using the AIC System are gathered. Then a union of all the information requested in these PAC forms is made. A field is created for each element of information requested. For example, Field #1 contains the patient's first name, Field #2 contains the patient's last name, and so on. This is done until the "information fields" of the PAC forms for all of the insurance companies are included.

In order to increase the efficiency of the clerical staff at the provider's office, it is desirable to give them basically the same form to fill out every time, i.e., information is always in the same place on the form. To do this a template is created. What actually appears on the screen of the preparer is always the same. What changes is that any given insurance company will desire only a particular subset of the total number of fields. So if insurance company A is chosen, then fields 1, 2, 3, 7, 9, . . . have to be filled in, whereas, if insurance company B is chosen, then fields 2, 3, 4, 5, 7, 11, . . . have to be filled in. The fields not needed are automatically signified in some way by the AIC software, e.g., if insurance company A does not need Field #4 then that block on the screen is gray and can't be typed into (i.e., is "write protected"). Thus a "customized claim form" is provided for every insurance company based on a single, universal compilation of fields. As described below, what allows this method to work is that there is AIC software at the insurance company that has been coordinated with the AIC software at the providers office.

The AIC Software GUI asks for the name of the insurance company, which can be typed in or selected from a directory. Once the insurance company has been identified, the fields needed to complete the insurance company's PAC form are displayed on the screen 212 of the service provider's computer system 210. The AIC software advantageously can automatically fill in all the parts of the form that are specific to the service provider, e.g., name, address, Provider Identification Number (PIN), etc. It is estimated that this alone eliminates 20% of the work needed to fill out the PAC form. An electronic signature could advantageously be added at this time for the service provider or could be added as part of the final review and approval before the completed PAC application is transmitted.

Needed patient information is then entered into the PAC form on the computer screen 212, preferably while the patient is still in the office, and a provider Document Identification Number (PDIN) can be used to label the form, if so desired. This is now a computer file identified as referring to the patient. It should be noted that some form of signature can be provided in the appropriate field. As an example, a special electronic pad and pen can be used such that when the patient signs on the pad his signature is affixed to the electronic PAC form.

During step S104, the patient's x-ray is digitized. In an exemplary case, there is a scanner 220, i.e., digitizer, connected to the service provider's computer system running the AIC software. The patient's x-ray is scanned and converted into a series of ordered numbers (i.e., a bit map of the x-ray image) and stored. It should be noted that these stored series of numbers can be reconstructed by the computer system to display the x-ray on a computer monitor, i.e., the bit map can be used to reconstruct a raster image of the x-ray for display.

It will be appreciated that the AIC software advantageously can be written to minimize the time needed to scan the x-ray. In an exemplary case, the operator can specify the type of x-ray or x-rays that are being scanned. This is done so that blank areas are not being digitized and added to the patient's file. It will be noted that this will also save on transmission time to the insurance company. Further, as will be readily appreciated by those skilled in the art, the text and image data comprising the file can be encoded and compressed in any manner well known in the art in order to minimize data storage and transmitting claimed requirements. In addition, security measures can be taken so that only authorized persons can access the claims.

It should also be mentioned that steps S103 and S104 need not be performed in any particular order. In an exemplary case, the patient's x-ray may be digitized before the PAC form is called up on the computer screen 212 and completed.

During step S105, the PAC application is formed from the electronic PAC form and the digitized patient's x-ray. It should be noted that the present invention is not limited to a particular format for the PAC application. For example, the format of the PAC application advantageously may consist of a text file and an associated digitized image file. It should be noted that in this case the text and image files will be transmitted seriatim. For that reason, the text file (i.e., the PAC form) and the image file (i.e., the digitized x-ray) must cross reference one another (i.e., be correlated) so that these files can be continuously associated with one another after transmission to the insurance company. If the attachment is simply additional ASCII text, e.g., Operating Room Notes, then the only step necessary is to transfer the additional ASCII text into the integrated file format. Once in the integrated file format, all processing is the same as if the file contained an image attachment.

In an alternative exemplary case, the PAC application advantageously can be prepared according to the Graphic Interchange Format™ (GIF) specification, which specification is the intellectual property of CompuServe Incorporated. In order to form the PAC application, the digitized x-ray is converted to a GIF image file. It will be appreciated that the GIF image file advantageously can include one or more blocks of textual data denoted by a comment extension, as described in Version 89a of the GRAPHICS INTERCHANGE FORMAT documentation published by CompuServe, Inc. It should be noted that since the textual information corresponding to the data needed to complete the PAC form is included in the GIF image file comments, the possibility of file separation and consequent mishandling or mismatching of the separate components of the PAC application is virtually eliminated. Alternatively, the TIFF standard format advantageously can also be used to co-join field and digital image data.

It will also be appreciated that the concept of embedding comments into the GIF or TIFF image file format is a standard practice employed by those of ordinary skill in the art of graphic image preparation, e.g., by photographers and digital artists who wish to identify their works. However, it should also be noted that the use of a comment block storing data fields used in reconstructing a completed form, e.g., a completed PAC form, has never before been described or suggested. Furthermore, since the technique described above is a novel solution to electronically forwarding an insurance claim form and an associated attachment as one, the use of the comment block to store the PAC form field data is likewise a unique and novel aspect according to the present invention.

In yet another alternative exemplary case, the digitized x-ray is automatically added (inserted) to the electronic form by the service provider's AIC software and forms a single computer file, as depicted in FIG. 5B. It should be noted that the non-text portion of the PAC application is labeled with the same provider Document Identification Number (DIN) as used on the text portion, i.e., the electronic PAC form. These two objects together now form the patient record, i.e., the patient's PAC application. The PAC application is now ready to be sent to the insurance company.

During step S106, the service provider's office staff then transmits the completed PAC application to the insurance company. For example, when the transmission icon of the GUI AIC software running on the service provider's computer system 210 is activated (e.g., "clicked" on), the following substeps are automatically executed:

(a) A check is first performed to ensure that the PAC application has been completely filled out. In the event that problems and/or errors are noted by the AIC software, the system user is notified of the error by an appropriate annunciator, e.g., the suspect area can be highlighted and a message concerning the problem and/or error could be generated and displayed on the monitor;

(b) A hard copy of the PAC application is printed out, if desired, by the service provider. The hard copy may advantageously be placed in the patient's permanent file;

(c) Moreover, and more importantly, the completed PAC application is archived in the service provider's computer system 210, 240. It will be appreciated that this archive copy can be accessed in several ways such as by patient name, social security number, document identification number, etc. That is, it can be accessed using any of the information that has been entered into the PAC form; and (d) The service provider's computer system establishes a connection with the on-line service 400 and transmits the patient's PAC application to the insurance companies e-mail address. See task T1 of FIG. 3A. It will be appreciated that the e-mail addresses of all the insurance companies have been stored in the AIC software residing in the memory of computer system 210. Advantageously, the PAC application can be transmitted immediately or can be scheduled for transmission at a convenient time, i.e., can be transmitted after all of the PAC applications and other forms have been prepared for the day. Preferably, the AIC software on the service provider's computer system 210 keeps a record of when the PAC application was sent. In addition, the AIC software maintains and uses the proper protocols so that when the PAC application reaches the intended insurance company, it arrives there with the alpha-numeric portion of computer file intact, i.e., the information is stored in fields that can be read by the corresponding AIC software module in the computer system 310 at the insurance company.

It should be noted that the specific transmission path taken by the PAC application from the service provider's computer system 210 to the computer system 310 maintained by the insurance company is not an essential limitation of the novel system and corresponding operating method according to a preferred embodiment of the present invention. The only requirement of a transmission path is that it maintain the digital integrity of the PAC application computer file. Thus, the patient's PAC application can be sent to the insurance company in several ways using modems 216 and 316, including via normal phone service, an on-line service, or bulk data transmission lines.

In an alternative exemplary case, the completed PAC applications may even be transferred to tape and then sent through the U.S. Postal Service 100 of FIG. 1 to the insurance company's mailroom 320. For purposes of the discussion which follows, only the exemplary case in which the PAC application is transmitted via the on-line service 400 is described in any detail.

Figure 6A:
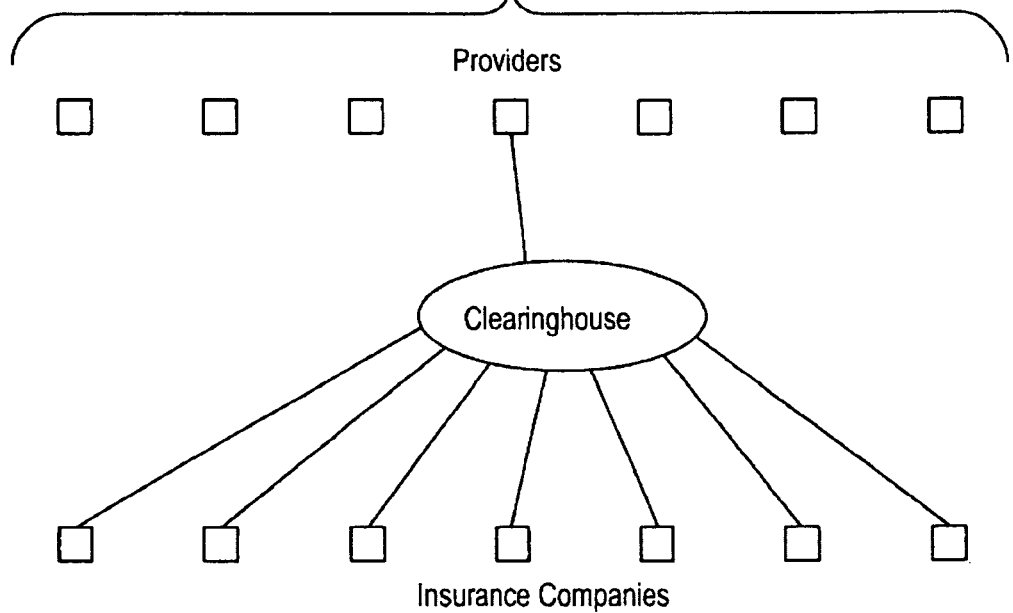
FIGS. 6A and 6B illustrate clearinghouse and non-clearinghouse networks, respectively, connecting service providers and insurance companies.

One of the beneficial aspects of the present invention is provided by the combination of the customizable claim form on the service provider's computer 210 and the use of any non-restrictive communications channel, i.e., the insurance companies are able to freely modify information requirements demanded of the service providers. Existing electronic claims processing systems, such as NEIC, are based on a clearinghouse concept, as illustrated in FIG. 6A. In a clearing house system, all claims enter the clearinghouse computer(s), are manipulated, and then are transmitted to the appropriate insurance company. One consequence of the clearinghouse architecture is that it puts a constraint on the insurance company to use a standardized claim form. The individual insurance companies have no control of the information content in the form. Moreover, because the claim form is standardized, changes are very difficult to make, i.e., any change would require all member insurance companies to make the change together.

In contrast, placing AIC software packages in the providers' offices and in the insurance company processing centers, where the packages are coordinated with one another, allows every payer to transmit claim form updates to every provider. There is no central computer that manipulates the claim forms. In the provider's office, the change would be reflected primarily in changes to the number of fields needing information and, rarely, in the addition of a new field to be completed by the provider.

Figure 6B:
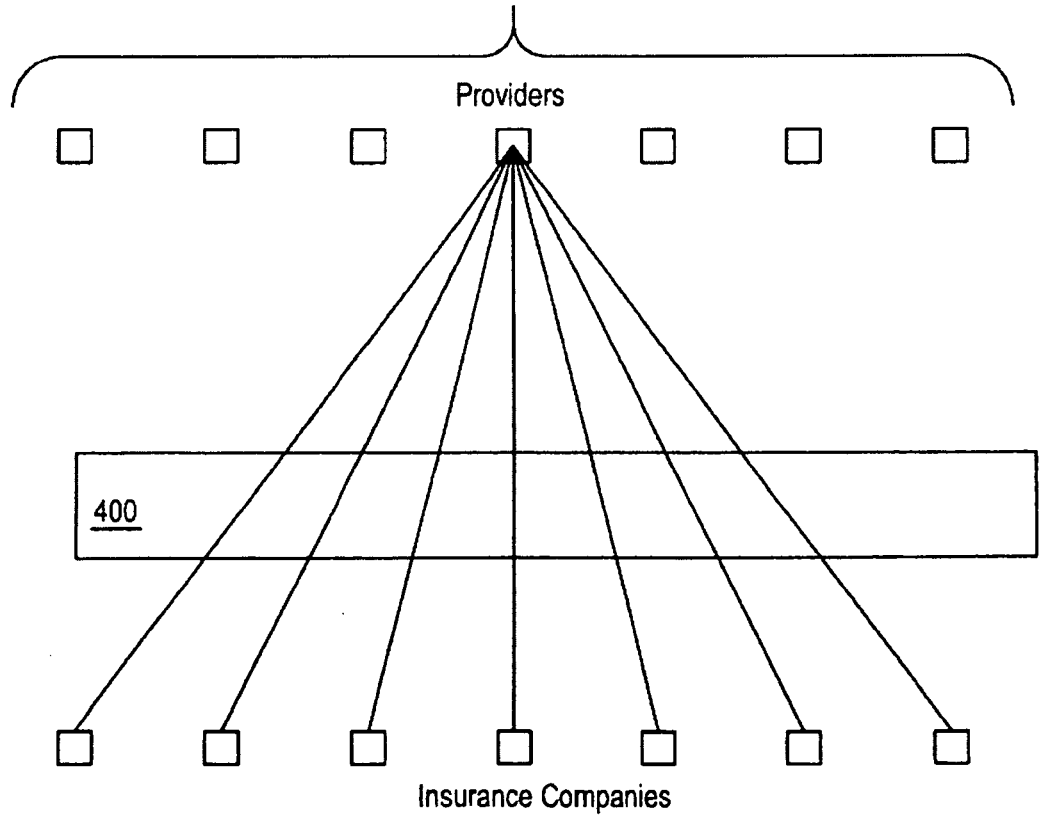

As illustrated in FIG. 6B, the interchange between the provider's office and the insurance company(ies) advantageously can be performed using an online service or Internet Service Provider (ISP), providing that the service provider permits 8-bit file interchanges. In that case, the update information could be transmitted to the provider when the provider dials into the online service. Thus, while it is true that transmission accomplished using e-mail involves an intermediary computer, the online service merely provides a mail box and places no conditions on the insurance information contained in the claim itself.

Advantageously, the non-clearinghouse architecture and coordinated AIC software package of the embodiment of FIG. 3A facilitates the provision of the customizable claim form. That is, each insurance company can determine the content of its own claim form. The packages used by the providers are instructed regarding the information content, protocols, etc. each insurance company wants its claim to have. It will be appreciated that the package at each insurance company is designed to accept only those claims that meet the specifications of the respective insurance company. In addition, if an insurance company wants to change the content of its claim form, it can do so independently of the other insurance companies.

Beneficially, the non-clearinghouse architecture of the embodiment of FIG. 3A reduces costs, allows for the direct digital interchange of data from one insurance company to another, and permits many different types of forms to be run off the same system, e.g. commercial insurance claims and workers' compensation claims can both be processed in the provider's office using the same customizable claim form. This produces a claims processing system which is more robust than anything on the market today.

During step S107, the PAC application is pre-processed by the value-added service provider 500. For example, the patient's PAC application can be accessed by the employees of the value-added service company to perform services for either the patient, the service provider, or the insurance company, or any combination thereof. See task T2 of FIG. 3A. These value-added services could include archiving of the patient's dental x-rays so that all records for a particular patient are centrally stored, screening of the entire PAC application for errors, compiling statistics on all PAC applications and, in some instances, even performing the review process for the insurance company.

Next, the insurance company accesses the PAC applications at the on-line service during step S108. In an exemplary case, each insurance company has an e-mail address specifically for the purpose of receiving PAC applications. An insurance company accesses its e-mail box and finds a waiting list of PAC applications which are subsequently downloaded to GUI-capable computer system 310. In a preferred embodiment as shown in FIG. 3A, the GUI-capable computer system 310 is separate from the claims management mainframe computer 350 of the insurance company 300. Preferably, the GUI-capable buffer computer system 310 is a personal computer (PC) or a PC server which advantageously can be operated in parallel with but separate from the insurance company's mainframe computer 350.

In an exemplary case, this buffer computer 310 is part of a local area network (LAN) 313, which is connected by high bandwidth cables to personal computers or other GUI-capable terminals 311, 312 at the desks 360 and 370 of the individual reviewing dentists and claims adjusters, respectively. It should be noted that the necessary AIC software has been loaded onto the server 310 and onto the individual personal computers 311, 312. Preferably, once the patient's PAC application has been received, the system's AIC software at either the value-added service provider 500 or the insurance company's computer 310 automatically notifies the referring service provider that the PAC application has been received for processing, e.g., using a conventional e-mail message.

At step S109, the reviewing dentist calls up the PAC application, in an exemplary case, from the server 310 to a personal computer 311, each of which is running the appropriate AIC software, via the LAN 313. See task T3 in FIG. 3A. It should be noted that some small insurance companies may not even require server-LAN 310, 313 system discussed above, but just a single PC that will incorporate the functions of the elements 310, 311, 312, and 313. In any event, the reviewing dentist calls up a patient's PAC application on his personal computer 311. When this happens, the system AIC software automatically inserts the insurance company's Predetermination Form into this file. The installed AIC software advantageously can automatically transfer whatever information from the PAC application to the Predetermination form that is useful in completing the Predetermination form, e.g., repetitive information/fields. For instance, the service provider's Document Identification Number (PDIN) and the Provider Identification Number (PIN) can be transferred automatically to the Predetermination form. In addition, the AIC software can be written to display the information in the PAC form on the screen 311 in exactly the way that this particular insurance company wants it displayed.

With the AIC system described above, the use of "fields," the customizable claim form, and the placing of coordinated AIC software at both the service provider's office and the insurance company, has eliminated the need for standardized forms. The result is that each insurance company gets exactly the information it wants and has it displayed in exactly the way it wants. Thus, the compromise of a standardized claim form as is required with the present NEIC system is avoided.

In an exemplary case, the reviewing dentist is provided with three monitors or a large graphics-capable monitor having a multi-page display mode, on which can be displayed the three pages of the patient file. It will be appreciated that this configuration is optimized to facilitate rapid review of the PAC application. The reviewing dentist enters an Insurance Company Document Identification Number (DIN) at this point, which number is affixed to all three pages of the patient's file.

During step S110, the reviewing dentist reviews the PAC application. More specifically, the review process consists of a review of the medical facts or evidence (i.e., the text and x-ray information in the PAC application), as well as a review of the patient's insurance policy. Once the reviewing dentist has made his analysis, he goes to the Predetermination form, i.e., the third page, and enters the required information to either approve or disapprove the procedure during step S111. The specific details regarding the information provided by the reviewing dentist will depend on the procedures established at each individual insurance company. Either the reviewing dentist or another person, e.g., a claims adjuster, will do the review of the patient's insurance policy.

Advantageously, there are several ways to gain access to this information. First, the server 310 can have information on every policy holder loaded into its memory. Second, the benefits reviewer, i.e., either the reviewing dentist or the claims adjuster, can have another monitor 351, 352 on his desk that is connected to the company mainframe computer 350. Thus, all that the benefits reviewer must do is type in the patient's insurance ID number and his benefits sheet will appear. The benefits reviewer then reads off the information that must be entered in the Predetermination form and enters the information into the GUI-capable computer system 310/311/312 during step S111. It should again be noted that there is no electronic connection, in the preferred embodiment, between the mainframe computer 350 and the server 310. The reviewer can, at this time, also enter whatever information is deemed necessary by that particular insurance company into the mainframe computer 350. See task T4 in FIG. 3A.

At this point, the Predetermination form is ready to be sent to the referring service provider. When the transmit icon on the computer screen of the benefit reviewer's GUI-capable computer system is activated (e.g., by being "clicked" on), the following substeps are automatically performed:

(a) First, a check is performed to verify that the Predetermination form has been completely and properly filled out. If errors are detected, the AIC software notifies the operator via an appropriate annunciator;

(b) The Predetermination form and the patient's PAC application are downloaded to the buffer computer 310. See task T5 of FIG. 3A. From this platform, the company accesses the on-line service 400 and transmits the Predetermination form, i.e., just the information "fields," to the service provider's e-mail address, which is stored in the memory of server 310. See task T6 of FIG. 3A. In the AIC software, records are kept as to which PAC applications have been sent and when and to whom. The proper protocols are used so that when the application reaches the service provider, it arrives there as a computer readable file, i.e., the information is stored in "fields" that can be read by the AIC software at both the insurance company and the service provider's office;

(c) A hard copy of the Predetermination form and x-ray are printed, if desired, by the insurance company, see task T7 of FIG. 3A;

(d) The complete patient file is archived in the insurance company's computer system 310, 340, if desired. See task T8 of FIG. 3A. Otherwise, just the electronic Predetermination form and the PAC application are saved; and (e) The entire three page patient file is now cleared from the reviewing dentist's display 311 and the AIC software prompts the reviewing dentist as to whether another patient file should be accessed.

During step S112, the service provider accesses his e-mail address with the on-line service 400. All Predetermination forms which have been received are automatically delivered to the service provider's computer system 210 for insertion into the appropriate patient file. The service provider then reviews the Predetermination forms. Upon evaluating the decision of the reviewing dentist, the service provider can either perform the procedure (if approved) or discuss the matter with the patient's insurance company (if not approved).

During step S113, the approved procedure is performed by the service provider. Once the approved procedure has been completed, the service provider preferably sends in the Final Payment Claim (FPC) form. In an exemplary case, this could be as simple as just filling out another section of the Predetermination form and signing it using the electronic signature pen, as discussed above. It should be noted that in FIG. 3A, this is labeled as P*. Alternatively, if the insurance company so desires, a separate form just for this purpose can be employed. This latter form, which advantageously is stored in the memory of the provider's computer, must have the Insurance Company's DIN for this particular patient's procedure and all other needed information transferred to it, which advantageously can all be done by the AIC system software at step S114. At step S115, the Final Payment Claim form is transmitted back to the insurance company. See task T9 of FIG. 3A. In an exemplary case, activating the transmit icon on the service provider's computer system 210, e.g., by "clicking" on it, automatically results in the execution of the following substeps:
  (a) A check is performed to see that the form has been completely and correctly filled out. If an error has occurred, the AIC software alerts the operator of the detected error;
  (b) A hard copy of the form is printed out, if desired, by the service provider;
  (c) The complete patient's electronic file is archived in the service provider's computer system 210, 240. It will be noted again that the patient's electronic file can be accessed by patient name, social security number, document identification number, etc.; and
  (d) The computer system 210 establishes a connection with the on-line service and transmits the patient's Final Payment Claim (FPC) form to the insurance company's e-mail address.

As previously discussed, the AIC software on the service provider's computer system 210 advantageously may include facilities for transmitting the Final Payment Claim form to the insurance company at a later time, e.g., for transmitting all of the days PAC application and FPC forms at one time.

It will also be noted, as discussed above, that the AIC software maintains records as to which claim form was sent and when it was sent to the insurance company. In an exemplary case, the e-mail address to which the Final Payment Claim form is sent is different from the address used in transmitting the PAC application. Since the Final Payment Claim form does not include a digitized image, i.e., a digitized x-ray, the insurance company may choose to have the Final Payment Claim form directed to an e-mail address accessible from the mainframe computer 350. If the insurance company's processing protocol requires an independent review of the PAC application, the Predetermination form and the Final Payment Claim form before payment can be authorized, the e-mail address will be accessed from, for example, the server 310 and not the mainframe computer 350, since the mainframe computer 350 is incompatible with the PAC application.

The insurance company then receives the Final Payment Claim forms during step S116 when it accesses its Final Payment Claim forms mail box. In an exemplary case, the computer system receiving the Final Payment Claim forms is not the claims management mainframe computer 350 of the insurance company but, rather, it is a personal computer or server 310 that is part of a parallel system having no electronic connection to the mainframe computer 350. This buffer computer 310 advantageously can be part of a LAN 313. The buffer computer 310 is connected by high bandwidth cables to the personal computers or GUI-capable terminals 312 located at the claims adjusters' desks. See task T10 of FIG. 3A. It should again be noted that the appropriate AIC software modules have been loaded onto both the server 310 and the personal computers 312.

The Final Payment Claim form is then reviewed during step S117. The adjuster reviewing the Final Payment Claim form can, if necessary, call up the PAC application from the memory of the server 310, since the original Insurance Company Document Identification Number for the corresponding PAC application was transferred to the Predetermination form and, thus, to the Final Payment Claim form. In addition, the adjuster can, if need be, call up the information on the insurance policy of the particular patient. The insurance company can either make this available in memory on the server 310 or the insurance company can provide the adjuster with a separate monitor 352 connected to the claims management mainframe computer 350.

Whatever internal paperwork is necessary to be filled out is automatically downloaded with the Final Payment Claim form itself by the appropriate AIC software module. Part of this paperwork will preferably be form(s) which must be completed so as to order a check issued to the service provider along with an Explanation of Benefits (EOB). Also at step S118, whatever information is necessary to be entered into the mainframe can be done through the use of the terminal 352.

Finally, upon activating the transmit icon on the insurance company's personal computer 312, the following substeps are automatically executed:
  (a) A check is again preformed to see that the form has been completely and correctly completed and the operator is notified if an error has occurred;
  (b) A hard copy of the form is printed out, if desired by the insurance company;
  (c) The complete patient file is archived in the insurance company's computer system, e.g., on the server. It should again be noted that the patient file can be accessed using the patient's name, social security number, or an assigned document identification number, etc.; and
  (d) A payment draft is issued, in the approved amount, to the service provider. This can be done through any number of methods, including printing a hard copy check and forwarding it through the U.S. postal service, electronic funds transfer, etc. Each form of payment will be accompanied with the normal description of the service to which these funds should be applied, i.e., the EOB (Explanation of Benefits).

Finally, it should again be mentioned that the exemplary preferred embodiment of the AIC system according to the embodiment of the present invention as depicted in FIG. 3A is a stand-alone system. Thus, it is independent of NEIC, mainframe computers 350, and existing claims management and practice management software. It will be appreciated that the stand-alone characteristic of the AIC system at the insurance company level enhances the reliability of the insurance company's hardware. In other words, the AIC system and software, which is independent of the mainframe computer 350, cannot cause mainframe system crashes that could interrupt the processing of other types of claims. Of course, alternative preferred embodiments of the present invention which integrate the AIC software with the claims management software may negate this particular advantage.

Embodiment of FIG. 3B

For the embodiment as shown in FIG. 3B, the overall system according to this embodiment of the present invention includes the computer components 200 located in the health care provider's office and the computer components 300 located on the premises of the insurance company. Infrastructure 400, which advantageously may be an existing on-line service company, is preferably used in the exemplary embodiment of the present invention to facilitate communication between the components 200 in the service provider's office and the components 300 at the insurance company. Preferably, components 500, which are located at a value-added service company, permit services ordered by the service provider, patient, or insurance company to be performed. It should be noted that the components 500 may duplicate a subset of the components 300 found at the insurance company and, for that reason, description of the components 300 alone will be provided below.

As shown in FIG. 3B, the components 200 include a personal computer 210 including a screen 212, a keyboard 214 and a modem 216, connected to a scanner 220, a printer 230 and an archiving device 240, e.g., a large memory for storage of digital information. Device 240 advantageously may be a writeable compact disc read only memory (CD-ROM), i.e., a so-called write once-read many (WORM) device, a hard disk drive, a tape back up device or a removable hard disk device. It should be recognized that the computer 210 advantageously can be a computer system including a central processing unit, a graphic display processor, the graphic display device 212, and several memories including both solid state memories and a hard disk drive. It should also be noted that the archive device 240 and one of the memories associated with computer 210 may be the same memory device.

Components 300 located at the insurance company include the previously described mainframe or legacy computer 350 and associated terminals 351, 352. In addition, a buffer computer 310, which may be a network server, includes a modem 316 and is connected to a printer 330 and a storage device 340. The printer 320 may provide copies of documents directly to the mailroom 320. Preferably, the computer 310 is connected to personal computers or work station terminals 311, 312 via a local area network (LAN) 313. The buffer computer 310 and the mainframe computer 350 are electronically connected to one another. The details of such a connection are well known to one of ordinary skill in the art and will not be described in greater detail.

The method for operating the system according to an embodiment of the present invention as depicted in FIG. 3B will now be described in detail.

The method starts at step S101 with the service provider's diagnosis that a costly procedure is necessary. It is then determined that the patient needs prior approval from his insurance company. During step S102, the patient is provided with an explanation of the procedure and a cost estimate for that procedure. The service provider and the patient then prepare the needed PAC Application.

During step S103, a member of the service provider's office staff accesses the Attachment Integrated Claims (AIC) software stored in non-volatile memory on the service provider's computer system 210, which software advantageously is Graphic User Interface (GUI) software. Preferably, this AIC software is written in C++, Visual Basic, or some other appropriate graphical programming language.

It will be appreciated that commercial software packages, such as LOTUS NOTES™, have been designed with the capability of addressing combinations of text and graphics files. However, the purpose of these packages is to create an "environment" or "platform" in which specific applications can be developed. In contrast, the preferred embodiments according to the present invention are directed at providing integrated text and graphics files within a coherent system and methodology for addressing the specific needs of the work flow, preferably of a particular industry. That is, it is a particular application. It is possible, but not necessary, that the software needed to implement the preferred embodiments of the present invention can be developed within the frame work of the environment created by something such as LOTUS NOTES™. Alternatively, the software needed to implement the preferred embodiments of the present invention can be developed using JAVA™ appelets.

Contained within the AIC software are PAC forms for insurance companies using the AIC system. When one of these is opened it acts as a template upon which a new computer file will be based. This computer file will ultimately contain the patient's PAC Application.

It will be appreciated that the PAC form when displayed on the computer's screen 212 contains boxes, such as those depicted in FIGS. 5A and 5B, in which alpha-numeric characters can be entered so that, when the characters are entered in these boxes they are entered so as to fill a "field," a delimited alpha-numeric character string. Being a "field," the information denoted by the characters can be transferred to and used in completing other fields in related documents. Also, the information itself, or lack thereof, can be used as a logic control device, e.g., used to remind the preparer that critical information has not been entered.

In the exemplary case being discussed, the PAC forms of many insurance companies have been encoded and stored in memory on the service provider's computer system 210. This can be advantageously done in the following way. The PAC forms for all the insurance companies using the AIC System are gathered. Then a union of all the information requested in these PAC forms is made. A field is created for each element of information requested. For example, Field #1 contains the patient's first name, Field #2 contains the patient's last name, and so on. This is done until the "information fields" of the PAC forms for all of the insurance companies are included.

In order to increase the efficiency of the clerical staff at the provider's office, it is desirable to give them basically the same form to fill out every time, i.e., information is always in the same place on the form. To do this a template is created. What actually appears on the screen of the preparer is always the same. What changes is that any given insurance company will desire only a particular subset of the total number of fields. So if insurance company A is chosen, then fields 1, 2, 3, 7, 9, . . . have to be filled in, whereas, if insurance company B is chosen, then fields 2, 3, 4, 5, 7, 11, . . . have to be filled in. The fields not needed are automatically signified in some way by the AIC software, e.g., if insurance company A does not need Field #4 then that block on the screen is gray and can't be typed into (i.e., is "write protected"). Thus a "customized claim form" is provided for every insurance company based on a single, universal compilation of fields. As described below, what allows this method to work is that there is AIC software at the insurance company that has been coordinated with the AIC software at the providers office.

The AIC Software GUI asks for the name of the insurance company, which can be typed in or selected from a directory. Once the insurance company has been identified, the fields needed to complete the insurance company's PAC form are displayed on the screen 212 of the service provider's computer system 210. The AIC software advantageously can automatically fill in all the parts of the form that are specific to the service provider, e.g., name, address, Provider Identification Number (PIN), etc. It is estimated that this alone eliminates 20% of the work needed to fill out the PAC form. An electronic signature could advantageously be added at this time for the service provider or could be added as part of the final review and approval before the completed PAC application is transmitted.

Needed patient information is then entered into the PAC form on the computer screen 212, preferably while the patient is still in the office, and a provider Document Identification Number (PDIN) can be used to label the form, if so desired. This is now a computer file identified as referring to the patient. It should be noted that some form of signature can be provided in the appropriate field. As an example, a special electronic pad and pen can be used such that when the patient signs on the pad his signature is affixed to the electronic PAC form.

During step S104, the patient's x-ray is digitized. In an exemplary case, there is a scanner 220, i.e., digitizer, connected to the service provider's computer system running the AIC software. The patient's x-ray is scanned and converted into a series of ordered numbers (i.e., a bit map of the x-ray image) and stored. It should be noted that these stored series of numbers can be reconstructed by the computer system to display the x-ray on a computer monitor, i.e., the bit map can be used to reconstruct a raster image of the x-ray for display.

It will be appreciated that the AIC software advantageously can be written to minimize the time needed to scan the x-ray. In an exemplary case, the operator can specify the type of x-ray or x-rays that are being scanned. This is done so that blank areas are not being digitized and added to the patient's file. It will be noted that this will also save on transmission time to the insurance company. Further, as will be readily appreciated by those skilled in the art, the text and image data comprising the file can be encoded and compressed in any manner well known in the art in order to minimize data storage and transmitting claimed requirements. In addition, security measures can be taken so that only authorized persons can access the claims.

It should also be mentioned that steps S103 and S104 need not be performed in any particular order. In an exemplary case, the patient's x-ray may be digitized before the PAC form is called up on the computer screen 212 and completed.

During step S105, the PAC application is formed from the electronic PAC form and the digitized patient's x-ray. It should be noted that the present invention is not limited to a particular format for the PAC application. For example, the format of the PAC application advantageously may consist of a text file and an associated digitized image file. It should be noted that in this case the text and image files will be transmitted seriatim. For that reason, the text file (i.e., the PAC form) and the image file (i.e., the digitized x-ray) must cross reference one another (i.e., be correlated) so that these files can be continuously associated with one another after transmission to the insurance company. If the attachment is simply additional ASCII text, e.g., Operating Room Notes, then the only step necessary is to transfer the additional ASCII text into the integrated file format. Once in the integrated file format, all processing is the same as if the file contained an image attachment.

In an alternative exemplary case, the PAC application advantageously can be prepared according to the Graphic Interchange Format™ (GIF) specification, which specification is the intellectual property of CompuServe Incorporated. In order to form the PAC application, the digitized x-ray is converted to a GIF image file. It will be appreciated that the GIF image file advantageously can include one or more blocks of textual data denoted by a comment extension, as described in Version 89a of the GRAPHICS INTERCHANGE FORMAT documentation published by CompuServe, Inc. It should be noted that since the textual information corresponding to the data needed to complete the PAC form is included in the GIF image file comments, the possibility of file separation and consequent mishandling or mismatching of the separate components of the PAC application is virtually eliminated. Alternatively, the TIFF standard format advantageously can also be used to cojoin field and digital image data.

It will also be appreciated that the concept of embedding comments into the GIF or TIFF image file format is a standard practice employed by those of ordinary skill in the art of graphic image preparation, e.g., by photographers and digital artists who wish to identify their works. However, it should also be noted that the use of a comment block storing data fields used in reconstructing a completed form, e.g., a completed PAC form, has never before been described or suggested. Furthermore, since the technique described above is a novel solution to electronically forwarding an insurance claim form and an associated attachment as one, the use of the comment block to store the PAC form field data is likewise a unique and novel aspect according to the present invention.

In yet another alternative exemplary case, the digitized x-ray is automatically added (inserted) to the electronic form by the service provider's AIC software and forms a single computer file, as depicted in FIG. 5B. It should be noted that the non-text portion of the PAC application is labeled with the same provider Document Identification Number (DIN) as used on the text portion, i.e., the electronic PAC form. These two objects together now form the patient record, i.e., the patient's PAC application. The PAC application is now ready to be sent to the insurance company.

During step S106, the service provider's office staff then transmits the completed PAC application to the insurance company. For example, when the transmission icon of the GUI AIC software running on the service provider's computer system 210 is activated (e.g., "clicked" on), the following substeps are automatically executed:

(a) A check is first performed to ensure that the PAC application has been completely filled out. In the event that problems and/or errors are noted by the AIC software, the system user is notified of the error by an appropriate annunciator, e.g., the suspect area can be highlighted and a message concerning the problem and/or error could be generated and displayed on the monitor;

(b) A hard copy of the PAC application is printed out, if desired, by the service provider. The hard copy may advantageously be placed in the patient's permanent file;

(c) Moreover, and more importantly, the completed PAC application is archived in the service provider's computer system 210, 240. It will be appreciated that this archive copy can be accessed in several ways such as by patient name, social security number, document identification number, etc. That is, it can be accessed using any of the information that has been entered into the PAC form; and (d) The service provider's computer system establishes a connection with the on-line service 400 and transmits the patient's PAC application to the insurance companies e-mail address. See task T1*a* of FIG. 3B. It will be appreciated that the e-mail addresses of all the insurance companies have been stored in the AIC software residing in the memory of computer system 210. Advantageously, the PAC application can be transmitted immediately or can be scheduled for transmission at a convenient time, i.e., can be transmitted after all of the PAC applications and other forms have been prepared for the day. Preferably, the AIC software on the service provider's computer system 210 keeps a record of when the PAC application was sent. In addition, the AIC software maintains and uses the proper protocols so that when the PAC application reaches the intended insurance company, it arrives there with the alpha-numeric portion of computer file intact, i.e., the information is stored in fields that can be read by the corresponding AIC software module in the computer system 310 at the insurance company.

It should be noted that the specific transmission path taken by the PAC application from the service provider's computer system 210 to the computer system 310 maintained by the insurance company is not an essential limitation of the novel system and corresponding operating method according to a preferred embodiment of the present invention. The only requirement of a transmission path is that it maintain the digital integrity of the PAC application computer file. Thus, the patient's PAC application can be sent to the insurance company in several ways using modems 216 and 316, including via normal phone service, an on-line service, or bulk data transmission lines.

In an alternative exemplary case, the completed PAC applications may even be transferred to tape or CD-ROM and then sent through the U.S. Postal Service 100 of FIG. 1 to the insurance company's mailroom 320. For purposes of the discussion which follows, only the exemplary case in which the PAC application is transmitted via the on-line service 400 is described in any detail.

One of the beneficial aspects of the present invention is provided by the combination of the customizable claim form on the service provider's computer 210 and the use of any non-restrictive communications channel, i.e., the insurance companies are able to freely modify information requirements demanded of the service providers. Existing electronic claims processing systems, such as NEIC, are based on a clearinghouse concept, as illustrated in FIG. 6A. In a clearing house system, all claims enter the clearinghouse computer(s), are manipulated, and then are transmitted to the appropriate insurance company. One consequence of the pure clearinghouse architecture is that it puts a constraint on the insurance company to use a standardized claim form. The individual insurance companies have little or no control of the information content in the form. Moreover, because the claim form is standardized, changes are very difficult to make, i.e., any change requires that all member insurance companies make the change together.

In contrast, placing AIC software packages in the providers' offices and in the insurance company processing centers, where the packages are coordinated with one another, allows every payer to transmit claim form updates to every provider. There is no central computer that manipulates the claim forms. In the provider's office, the change would be reflected primarily in changes to the number of fields needing information and, rarely, in the addition of a new field to be completed by the provider.

As illustrated in FIG. 6B, the interchange between the provider's office and the insurance company(ies) advantageously can be performed using an online service or Internet Service Provider (ISP), providing that the service provider permits 8-bit file interchanges. In that case, the update information could be transmitted to the provider when the provider dials into the online service. Thus, while it is true that transmission accomplished using e-mail involves an intermediary computer, the online service merely provides a mail box and places no conditions on the insurance information contained in the claim itself.

Advantageously, the non-clearinghouse architecture and coordinated AIC software package of the embodiment of FIG. 3B facilitates the provision of the customizable claim form. That is, each insurance company can determine the content of its own claim form. The packages used by the providers are instructed regarding the information content, protocols, etc. each insurance company wants its claim to have. It will be appreciated that the package at each insurance company is designed to accept only those claims that meet the specifications of the respective insurance company. In addition, if an insurance company wants to change the content of its claim form, it can do so independently of the other insurance companies.

Beneficially, the non-clearinghouse architecture reduces costs, allows for the direct digital interchange of data from one insurance company to another, and permits many different types of forms to be run off the same system, e.g. commercial insurance claims and workers' compensation claims can both be processed in the provider's office using the same customizable claim form. This produces a claims processing system which is more robust than anything on the market today.

During step S107, the PAC application is pre-processed by the value-added service provider 500. For example, the patient's PAC application can be accessed by the employees of the value-added service company to perform services for either the patient, the service provider, or the insurance company, or any combination thereof. See task T2 of FIG. 3B. These value-added services could include archiving of the patient's dental x-rays so that all records for a particular patient are centrally stored, screening of the entire PAC application for errors, compiling statistics on all PAC applications and, in some instances, even performing the review process for the insurance company.

Next, the insurance company accesses the PAC applications at the on-line service during step S108. In an exemplary case, each insurance company has an e-mail address specifically for the purpose of receiving PAC applications. An insurance company accesses its e-mail box and finds a waiting list of PAC applications which are subsequently downloaded to GUI-capable computer system 310. In a preferred embodiment as shown in FIG. 3B, the GUI-capable computer system 310 advantageously is connected to the claims management mainframe computer 350 of the insurance company 300. Preferably, the GUI-capable buffer computer system 310 is a personal computer (PC) or a PC server which advantageously can be operated in parallel with but separate from the insurance company's mainframe computer 350; data, however, beneficially can be interchanged between the buffer computer system 310 and the mainframe computer 350. In an exemplary case, as the personnel at the insurance company 300 apply an insurance company document identification number (DIN) to each received PAC Application, the field data contained therein is copied by the buffer computer system 310 and transmitted to the mainframe computer 350. See task T1*b* of FIG. 3B.

Alternatively, the entire PAC application advantageously could be copied by the buffer computer system 310 and downloaded to the mainframe computer 350, where the image portion of the PAC application then can be removed from the mainframe's memory. This approach employs basically the same distribution of information, i.e., text form in the mainframe 350 and field data and images in the buffer computer system 310.

In an exemplary case, this buffer computer 310 is part of a local area network (LAN) 313, which is connected by high bandwidth cables to personal computers or other GUI-capable terminals 311, 312 at the desks 360 and 370 of the individual reviewing dentists and claims adjusters, respectively. It should be noted that the necessary AIC software has been loaded onto the server 310, the individual personal computers 311, 312, and the mainframe 350. Preferably, once the patient's PAC application has been received, the system's AIC software at either the value-added service provider 500 or the insurance company's computer 310 automatically notifies the referring service provider that the PAC application has been received for processing, e.g., using a conventional e-mail message.

At step S109, the reviewing dentist calls up the graphics portion of the PAC application, in an exemplary case, from the server 310 to a personal computer 311, each of which is running the appropriate AIC software, via the LAN 313 using the assigned DIN. See task T3 in FIG. 3B. The reviewing dentist then calls up the text portion of the PAC application from the mainframe computer 350 using the terminal 351. See task T4 in FIG. 3B. It will be appreciated that the sequence can be reversed at the reviewing dentist's option. It should be noted that some small insurance companies may not even require server-LAN 310, 313 system discussed above, but just a single PC that will incorporate the functions of the elements 310, 311, 312, and 313. In any event, the reviewing dentist calls up a patient's PAC application using both his personal computer 311 and terminal 351. When this happens, the system AIC software automatically generates the insurance company's Predetermination Form on one of the two screens 311, 351. The installed AIC software advantageously can automatically transfer whatever information from the PAC application to the Predetermination form that is useful in completing the Predetermination form, e.g., repetitive information/fields. For instance, the service provider's Document Identification Number (PDIN) and the Provider Identification Number (PIN) can be transferred automatically to the Predetermination form. In addition, the AIC software can be written to display the information in the PAC form on the screen 351 in exactly the way that this particular insurance company wants it displayed.

In a alternative implementation, a single monitor on the computer 311 supporting multiple windows, at least one of which runs terminal emulation software for displaying the output of the mainframe computer 350, could advantageously be used to display both parts of the PAC application.

With the AIC system described above, the use of "fields," the customizable claim form, and the placing of coordinated AIC software at both the service provider's office and the insurance company, has eliminated the need for standardized forms. The result is that each insurance company gets exactly the information it wants and has it displayed in exactly the way it wants. Thus, the compromise of a standardized claim form as is required with the present NEIC system is avoided.

In an exemplary case, the reviewing dentist is provided with three monitors or a large graphics-capable monitor having a multi-page display mode, on which can be displayed the three pages of the patient file. It will be appreciated that this configuration is optimized to facilitate rapid review of the PAC application. The reviewing dentist enters an Insurance Company Document Identification Number (DIN) at this point, which number is affixed to all three pages of the patient's file.

During step S110, the reviewing dentist reviews the PAC application. More specifically, the review process consists of a review of the medical facts or evidence (i.e., the text and x-ray information in the PAC application), as well as a review of the patient's insurance policy. Once the reviewing dentist has made his analysis, he goes to the Predetermination form, i.e., the third page, and enters the required information to either approve or disapprove the procedure during step S111. The specific details regarding the information provided by the reviewing dentist will depend on the procedures established at each individual insurance company. Either the reviewing dentist or another person, e.g., a claims adjuster, will do the review of the patient's insurance policy.

Advantageously, there are several ways to gain access to this information. First, the server 310 can have information on every policy holder loaded into its memory. Second, the benefits reviewer, i.e., either the reviewing dentist or the claims adjuster, can have another monitor 351, 352 on his desk that is connected to the company mainframe computer 350. Thus, all that the benefits reviewer must do is select the patient's insurance ID number and his benefits sheet will appear. The benefits reviewer then reads off the information that must be entered in the Predetermination form and enters the information into the either the GUI-capable computer system 310/311/312 or the mainframe computer 350 during step S111. It should again be noted that there is an electronic connection, in the embodiment of FIG. 3B, between the mainframe computer 350 and the server 310. Whatever information is deemed necessary by that particular insurance company to complete the Predetermination form can be transferred between the mainframe computer 350 and the buffer computer system 310 by entering data on one of the terminals 311, 351. See, for example, task T5 in FIG. 3B.

At this point, the Predetermination form is ready to be sent to the referring service provider. When the transmit icon on the computer screen of the benefit reviewer's GUI-capable computer system 311, for example, is activated (e.g., by being "clicked" on), the following substeps are automatically performed:

(a) First, a check is performed to verify that the Predetermination form has been completely and properly filled out. If errors are detected, the AIC software notifies the operator via an appropriate annunciator;

(b) The Predetermination form and the patient's PAC application are downloaded to the buffer computer 310. See task T5*a* of FIG. 3B. From this platform, the company accesses the on-line service 400 and transmits the Predetermination form, i.e., just the information "fields," to the service provider's e-mail address, which is stored in the memory of server 310. See task T6 of FIG. 3B. In the AIC software, records are kept as to which PAC applications have been sent and when and to whom. The proper protocols are used so that when the application reaches the service provider, it arrives there as a computer readable file, i.e., the information is stored in "fields" that can be read by the AIC software at both the insurance company and the service provider's office;

(c) A hard copy of the Predetermination form and x-ray are printed, if desired, by the insurance company, see task T7 of FIG. 3B;

(d) The complete patient file is archived in the insurance company's computer system 310, 340, if desired. See task T8 of FIG. 3B. Otherwise, just the electronic Predetermination form and the PAC application are saved; and (e) The entire three page patient file is now cleared from the reviewing dentist's displays 311, 351 and the AIC software prompts the reviewing dentist as to whether another patient file should be accessed.

During step S112, the service provider accesses his e-mail address with the on-line service 400. All Predetermination forms which have been received are automatically delivered to the service provider's computer system 210 for insertion into the appropriate patient file. The service provider then reviews the Predetermination forms. Upon evaluating the decision of the reviewing dentist, the service provider can either perform the procedure (if approved) or discuss the matter with the patient's insurance company (if not approved).

During step S113, the approved procedure is performed by the service provider. Once the approved procedure has been completed, the service provider preferably sends in the Final Payment Claim (FPC) form. In an exemplary case, this could be as simple as just filling out another section of the Predetermination form and signing it using the electronic signature pen, as discussed above. It should be noted that in FIG. 3B, this is labeled as P*. Alternatively, if the insurance company so desires, a separate form just for this purpose can be employed. This latter form, which advantageously is the same customizable claim form discussed above, is stored in the memory of the provider's computer, must have the Insurance Company's DIN for this particular patient's procedure and all other needed information transferred to it, which advantageously can all be done by the AIC system software at step S114. At step S115, the Final Payment Claim form is transmitted back to the insurance company. See task T9 of FIG. 3B. In an exemplary case, activating the transmit icon on the service provider's computer system 210, e.g., by "clicking" on it, automatically results in the execution of the following substeps:

(a) A check is performed to see that the form has been completely and correctly filled out. If an error has occurred, the AIC software alerts the operator of the detected error;

(b) A hard copy of the form is printed out, if desired, by the service provider;

(c) The complete patient's electronic file is archived in the service provider's computer system 210, 240. It will be noted again that the patient's electronic file can be accessed by patient name, social security number, document identification number, etc.; and (d) The computer system 210 establishes a connection with the on-line service and transmits the patient's Final Payment Claim (FPC) form to the insurance company's e-mail address.

As previously discussed, the AIC software on the service provider's computer system 210 advantageously may include facilities for transmitting the Final Payment Claim form to the insurance company at a later time, e.g., for transmitting all of the days PAC application and FPC forms at one time.

It will also be noted, as discussed above, that the AIC software maintains records as to which claim form was sent and when it was sent to the insurance company. In an exemplary case, the e-mail address to which the Final Payment Claim form is sent is different from the address used in transmitting the PAC application. Since the Final Payment Claim form does not include a digitized image, i.e., a digitized x-ray, the insurance company may choose to have the Final Payment Claim form directed to an e-mail address accessible from the mainframe computer 350. If the insurance company's processing protocol requires an independent review of the PAC application, the Predetermination form and the Final Payment Claim form before payment can be authorized, the e-mail address advantageously can be accessed from either the server 310 or the mainframe computer 350, since these two computer systems are electrically coupled at the insurance company 300.

The insurance company then receives the Final Payment Claim forms during step S116 when it accesses its Final Payment Claim forms mail box. In an exemplary case, the computer system receiving the Final Payment Claim forms is not the claims management mainframe computer 350 of the insurance company but, rather, it is a personal computer or server 310 that is part of a parallel system having an electronic connection to the mainframe computer 350. This buffer computer 310 advantageously can be part of a LAN 313. The buffer computer 310 is connected by high bandwidth cables to the personal computers or GUI-capable terminals 312 located at the claims adjusters' desks. See task T10 of FIG. 3B. It should again be noted that the appropriate AIC software modules have been loaded onto the server 310, the personal computers 312 and the mainframe computer 350. It will be appreciated that the information entered in computer 312 advantageously can be automatically transferred to the mainframe 350 through the transmission path including the computer 312, the buffer computer 310 and the electronic connection to the mainframe computer 350.

The Final Payment Claim form is then reviewed during step S117. The adjuster reviewing the Final Payment Claim form can, if necessary, call up the PAC application from the memory of the server 310, since the original Insurance Company Document Identification Number for the corresponding PAC application was transferred to the Predetermination form and, thus, to the Final Payment Claim form. In addition, the adjuster can, if need be, call up the information on the insurance policy of the particular patient stored in mainframe computer 350 via terminal 352. Preferably, the insurance company provides the adjuster with a separate monitor 352 connected to the claims management mainframe computer 350.

Whatever internal paperwork is necessary to be filled out is automatically downloaded with the Final Payment Claim form itself by the appropriate AIC software module. Part of this paperwork will preferably be form(s) which must be completed so as to order a check issued to the service provider along with an Explanation of Benefits (EOB). Also at step S118, whatever information is necessary to be entered into the mainframe 350 can be entered directly through the use of the terminal 352 or indirectly through computer 312, the buffer computer 310 and the electronic connection to the mainframe computer 350.

Finally, upon activating the transmit icon on the insurance company's personal computer 312, for example, the following substeps are automatically executed:

(a) A check is again preformed to see that the form has been completely and correctly completed and the operator is notified if an error has occurred;

(b) A hard copy of the form is printed out, if desired by the insurance company;

(c) The complete patient file is archived in the insurance company's computer system, e.g., on the server. It should again be noted that the patient file can be accessed using the patient's name, social security number, or an assigned document identification number, etc.; and (d) A payment draft is issued, in the approved amount, to the service provider. This can be done through any number of methods, including printing a hard copy check and forwarding it through the U.S. postal service, electronic funds transfer, etc. Each form of payment will be accompanied with the normal description of the service to which these funds should be applied, i.e., the EOB (Explanation of Benefits).

Figure 3C:
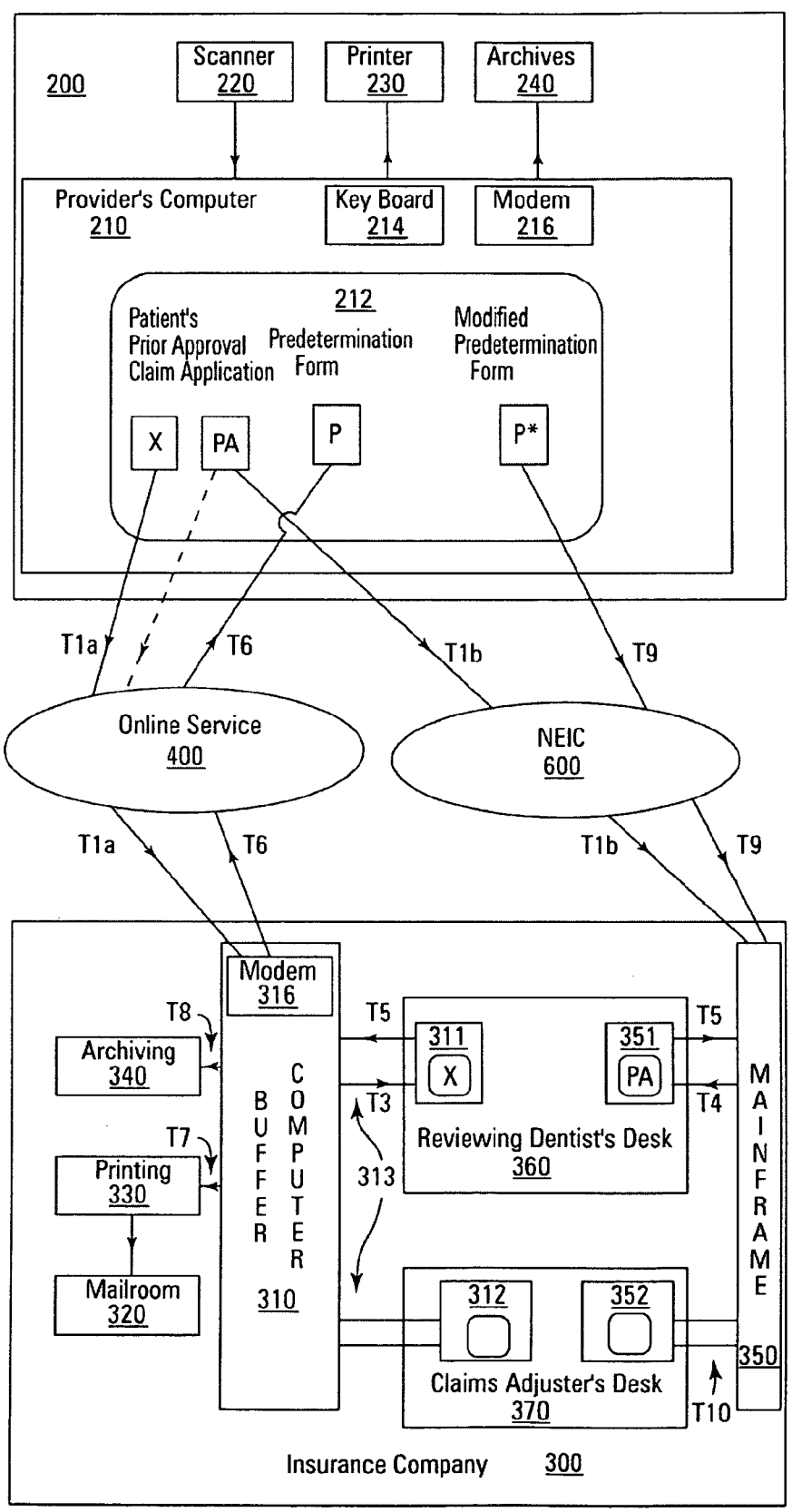
Figure 4:
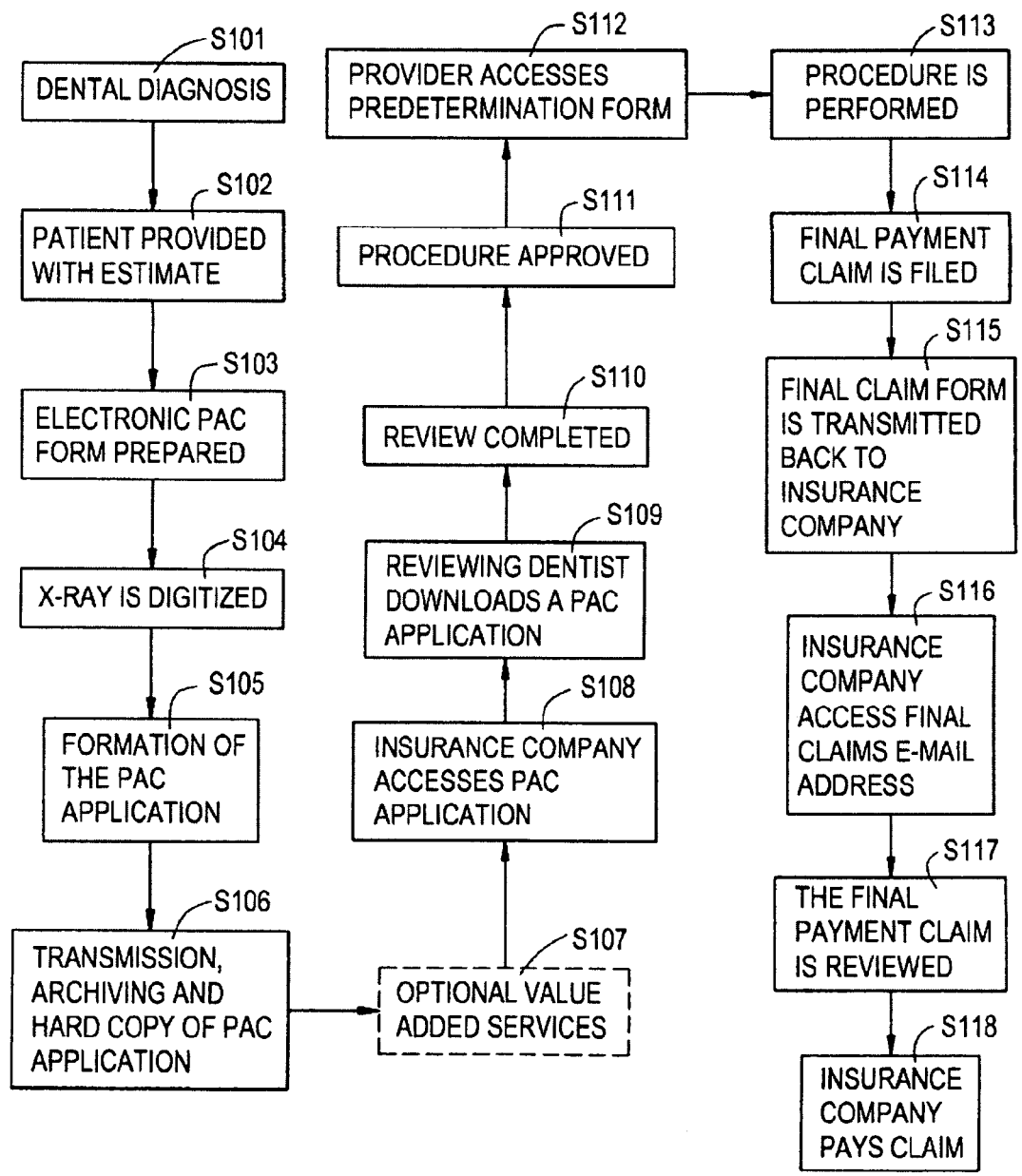
FIG. 4 is a detailed flow chart of the operational steps needed to operate the systems illustrated in FIGS. 3A-3C.

Embodiment of FIG. 3C

In the embodiment as shown in FIG. 3C, the overall system according to the present invention includes the computer components 200 located in the health care provider's office and the computer components 300 located on the premises of the insurance company. Infrastructure 400, which advantageously may be an existing on-line service company, and clearinghouse 600, e.g., NEIC, are preferably used in one embodiment of the present invention to facilitate communication between the components 200 in the service provider's office and the components 300 at the insurance company.

As shown in FIG. 3C, the components 200 include a personal computer 210 including a screen 212, a keyboard 214 and a modem 216, connected to a scanner 220, a printer 230 and an archiving device 240, e.g., a large memory for storage of digital information. Device 240 advantageously may be a writeable compact disc read only memory (CD-ROM), i.e., a so-called write once-read many (WORM) device, a hard disk drive, a tape back up device or a removable hard disk device. It should be recognized that the computer 210 advantageously can be a computer system including a central processing unit, a graphic display processor, the graphic display device 212, and several memories including both solid state memories and a hard disk drive. It should also be noted that the archive device 240 and one of the memories associated with computer 210 may be the same memory device.

Components 300 located at the insurance company include the previously described mainframe or legacy computer 350 and terminals 351, 352. In addition, a buffer computer 310, which may be a network server, includes a modem 316 and is connected to a printer 330 and a storage device 340. The printer 320 may provide copies of documents directly to the mailroom 320. Preferably, the computer 310 is connected to personal computers or work station terminals 311, 312 via a local area network (LAN) 313.

The method for operating the system according to the embodiment of the present invention as depicted in FIG. 3C will now be described in detail.

The method starts at step S101 with the service provider's diagnosis that a costly procedure is necessary. It is then determined that the patient needs prior approval from his insurance company. During step S102, the patient is provided with an explanation of the procedure and a cost estimate for that procedure. The service provider and the patient then prepare the needed PAC Application.

During step S103, a member of the service provider's office staff accesses the Attachment Integrated Claims (AIC) software stored in non-volatile memory on the service provider's computer system 210, which software advantageously is Graphic User Interface (GUI) software. Preferably, this AIC software is written in C++, Visual Basic, or some other appropriate graphical programming language.

It will be appreciated that commercial software packages, such as LOTUS NOTES™, have been designed with the capability of addressing combinations of text and graphics files. However, the purpose of these packages is to create an "environment" or "platform" in which specific applications can be developed. In contrast, the preferred embodiments according to the present invention are directed at providing integrated text and graphics files within a coherent system and methodology for addressing the specific needs of the work flow, preferably of a particular industry. That is, it is a particular application. It is possible, but not necessary, that the software needed to implement the preferred embodiments of the present invention can be developed within the frame work of the environment created by something such as LOTUS NOTES™. Alternatively, the software needed to implement the preferred embodiments of the present invention can be written as a JAVA™ appelet.

Contained within the AIC software are PAC forms for insurance companies using the AIC system. When one of these is opened it acts as a template upon which a new computer file will be based. This computer file will ultimately contain the patient's PAC Application.

It will be appreciated that the PAC form when displayed on the computer's screen 212 contains boxes, such as those depicted in FIGS. 5A and 5B, in which alpha-numeric characters can be entered so that, when the characters are entered in these boxes they are entered so as to fill a "field," a delimited alpha-numeric character string. Being a "field," the information denoted by the characters can be transferred to and used in completing other fields in related documents. Also, the information itself, or lack thereof, can be used as a logic control device, e.g., used to remind the preparer that critical information has not been entered.

In an exemplary case, the PAC forms of many insurance companies have been encoded and stored in memory on the service provider's computer system 210. This can be advantageously done in the following way. The PAC forms for all the insurance companies using the AIC System are gathered. Then a union of all the information requested in these PAC forms is made. A field is created for each element of information requested. For example, Field #1 contains the patient's first name, Field #2 contains the patient's last name, and so on. This is done until the "information fields" of the PAC forms for all of the insurance companies are included.

In order to increase the efficiency of the clerical staff at the provider's office, it is desirable to give them basically the same form to fill out every time, i.e., information is always in the same place on the form. To do this a template is created. What actually appears on the screen of the preparer is always the same. What changes is that any given insurance company will desire only a particular subset of the total number of fields. So if insurance company A is chosen, then fields 1, 2, 3, 7, 9 . . . have to be filled in, whereas, if insurance company B is chosen, then fields 2, 3, 4, 5, 7, 11, . . . have to be filled in. The fields not needed are automatically signified in some way by the AIC software, e.g., if insurance company A does not need Field #4 then that block on the screen is gray and can't be typed into (i.e., is "write protected"). Thus a "customizable claim form" is provided for every insurance company based on a single, universal compilation of fields. As described below, what allows this method to work is that there is AIC software at the insurance company that has been coordinated with the AIC software at the providers office.

The AIC Software GUI asks for the name of the insurance company, which can be typed in or selected from a directory. Once the insurance company has been identified, the fields needed to complete the insurance company's PAC form are displayed on the screen 212 of the service provider's computer system 210. The AIC software advantageously can automatically fill in all the parts of the form that are specific to the service provider, e.g., name, address, Provider Identification Number (PIN), etc. It is estimated that this alone eliminates 20% of the work needed to fill out the PAC form. An electronic signature could advantageously be added at this time for the service provider or could be added as part of the final review and approval before the completed PAC application is transmitted.

Needed patient information is then entered into the PAC form on the computer screen 212, preferably while the patient is still in the office, and a provider Document Identification Number (PDIN) can be used to label the form, if so desired. This is now a computer file identified as referring to the patient. It should be noted that some form of signature can be provided in the appropriate field. As an example, a special electronic pad and pen can be used such that when the patient signs on the pad his signature is affixed to the electronic PAC form.

During step S104, the patient's x-ray is digitized. In an exemplary case, there is a scanner 220, i.e., digitizer, connected to the service provider's computer system running the AIC software. The patient's x-ray is scanned and converted into a series of ordered numbers (i.e., a bit map of the x-ray image) and stored. It should be noted that these stored series of numbers can be reconstructed by the computer system to display the x-ray on a computer monitor, i.e., the bit map can be used to reconstruct a raster image of the x-ray for display.

It will be appreciated that the AIC software advantageously can be written to minimize the time needed to scan the x-ray. In an exemplary case, the operator can specify the type of x-ray or x-rays that are being scanned. This is done so that blank areas are not being digitized and added to the patient's file. It will be noted that this will also save on transmission time to the insurance company. Further, as will be readily appreciated by those skilled in the art, the text and image data comprising the file can be encoded and compressed in any manner well known in the art in order to minimize data storage and transmitting claimed requirements. In addition, security measures can be taken so that only authorized persons can access the claims.

It should also be mentioned that steps S103 and S104 need not be performed in any particular order. In an exemplary case, the patient's x-ray may be digitized before the PAC form is called up on the computer screen 212 and completed.

During step S105, the PAC application is formed from the electronic PAC form and the digitized patient's x-ray. It should be noted that the present invention is not limited to a particular format for the PAC application. For example, the format of the PAC application advantageously may consist of a text file and an associated digitized image file. It should be noted that in this case the text and image files will be transmitted seriatim. For that reason, the text file (i.e., the PAC form) and the image file (i.e., the digitized x-ray) must cross reference one another (i.e., be correlated) so that these files can be continuously associated with one another after transmission to the insurance company. If the attachment is simply additional ASCII text, e.g., Operating Room Notes, then the only step necessary is to transfer the additional ASCII text into the integrated file format. Once in the integrated file format, all processing is the same as if the file contained an image attachment.

In an alternative exemplary case, the PAC application advantageously can be prepared according to the Graphic Interchange Format™ (GIF) specification, which specification is the intellectual property of CompuServe Incorporated. In order to form the PAC application, the digitized x-ray is converted to a GIF image file. It will be appreciated that the GIF image file advantageously can include one or more blocks of textual data denoted by a comment extension, as described in Version 89a of the GRAPHICS INTERCHANGE FORMAT documentation published by CompuServe, Inc. It should be noted that since the textual information corresponding to the data needed to complete the PAC form is included in the GIF image file comments, the possibility of file separation and consequent mishandling or mismatching of the separate components of the PAC application is virtually eliminated. Alternatively, the TIFF standard format advantageously can also be used to co-join field and digital image data.

It will also be appreciated that the concept of embedding comments into the GIF or TIFF image file format is a standard practice employed by those of ordinary skill in the art of graphic image preparation, e.g., by photographers and digital artists who wish to identify their works. However, it should also be noted that the use of a comment block storing data fields used in reconstructing a completed form, e.g., a completed PAC form, has never before been described or suggested. Furthermore, since the technique described above is a novel solution to electronically forwarding an insurance claim form and an associated attachment as one, the use of the comment block to store the PAC form field data is likewise a unique and novel aspect according to the present invention.

In yet another alternative exemplary case, the digitized x-ray is automatically added (inserted) to the electronic form by the service provider's AIC software and forms a single computer file, as depicted in FIG. 5B. It should be noted that the non-text portion of the PAC application is labeled with the same provider Document Identification Number (PDIN) as used on the text portion, i.e., the electronic PAC form. These two objects together now form the patient record, i.e., the patient's PAC application. The PAC application is now ready to be sent to the insurance company.

During step S106, the service provider's office staff then transmits the completed PAC application to the insurance company. For example, when the transmission icon of the GUI AIC software running on the service provider's computer system 210 is activated (e.g., "clicked" on), the following substeps are automatically executed:

(a) A check is first performed to ensure that the PAC application has been completely filled out. In the event that problems and/or errors are noted by the AIC software, the system user is notified of the error by an appropriate annunciator, e.g., the suspect area can be highlighted and a message concerning the problem and/or error could be generated and displayed on the monitor;

(b) A hard copy of the PAC application is printed out, if desired, by the service provider. The hard copy may advantageously be placed in the patient's permanent file;

(c) Moreover, and more importantly, the completed PAC application is archived in the service provider's computer system 210, 240. It will be appreciated that this archive copy can be accessed in several ways such as by patient name, social security number, document identification number, etc. That is, it can be accessed using any of the information that has been entered into the PAC form; and (d) The service provider's computer system establishes a connection with the on-line service 400 and transmits the patient's PAC application to the insurance companies e-mail address. See task T1*a* of FIG. 3C. In addition, the selected portions of the field data, i.e., the PAC form, are transmitted to clearinghouse 600. See task T1*b* of FIG. 3C. It should be mentioned that only the digital attachment to the patient's PAC application advantageously need be transmitted to the insurance company 300 using the online service 400. However, since transmission of the entire PAC application insures that the complete PAC application is available to the insurance company, the provider's office 200 preferably transmits the entire PAC application to the insurance company 300.

It will also be appreciated that the e-mail addresses of all the insurance companies have been stored in the AIC software residing in the memory of computer system 210. Advantageously, the digital attachment and field data forming the PAC application can be transmitted immediately or can be scheduled for transmission at a convenient time, i.e., can be transmitted after all of the PAC applications and other forms have been prepared for the day. Preferably, the AIC software on the service provider's computer system 210 keeps a record of when the PAC application was sent. In addition, the AIC software maintains and uses the proper protocols so that when the PAC application reaches the intended insurance company, it arrives there with the alpha-numeric portion of computer file intact, i.e., the information is stored in fields that can be read by the corresponding AIC software module in the mainframe computer 350 at the insurance company 300.

It should be noted that the specific transmission path taken by the PAC application from the service provider's computer system 210 to the computer system 310 maintained by the insurance company is not an essential limitation of the novel system and corresponding operating method according to a preferred embodiment of the present invention. The only requirement of a transmission path is that it maintain the digital integrity of the PAC application computer file. Thus, the patient's PAC application can be sent to the insurance company in several ways using modems 216 and 316, including via normal phone service, the on-line service 400, or bulk data transmission lines.

In an alternative exemplary case, the completed PAC applications may even be transferred to tape or CD-ROM and then sent through the U.S. Postal Service 100 of FIG. 1 to the insurance company's mailroom 320. For purposes of the discussion which follows, only the exemplary case in which the digital attachment for the PAC application is transmitted via the on-line service 400 is described in any detail.

One of the beneficial aspects of the present invention is provided by the combination of the customizable claim form on the service provider's computer 210 and the use of any non-restrictive communications channel, i.e., the insurance companies are able to freely modify information requirements demanded of the service providers. Existing electronic claims processing systems, such as NEIC, are based on a clearinghouse concept, where all claims entering the clearinghouse computer(s), are manipulated, and then are transmitted to the appropriate insurance company. One consequence of the clearinghouse architecture alone is that it puts a constraint on the insurance company to use a standardized claim form. The individual insurance companies have no control of the information content in the form. Moreover, because the claim form is standardized, changes are very difficult to make, i.e., any change would require all member insurance companies to make the change together.

In contrast, placing AIC software packages in the providers' offices and in the insurance company processing centers, where the packages are coordinated with one another, allows every payer to transmit claim form updates to every provider. In the provider's office, the change would be reflected primarily in changes to the number of fields needing information and, rarely, in the addition of a new field to be completed by the provider. Transfer of this additional or supplemental information between the provider's office and the insurance company(ies) advantageously can be performed using an online service or Internet Service Provider (ISP), providing that the service provider permits 8-bit file interchanges. In that case, the update information could be transmitted to the provider when the provider dials into the online service.

Advantageously, the simultaneous use of both clearinghouse and non-clearinghouse architectures and coordinated AIC software packages of the embodiment of FIG. 3C facilitates the provision of the customizable claim form. That is, each insurance company can determine the content of its own claim form. The packages used by the providers are instructed regarding the information content, protocols, etc. each insurance company wants its claim to have. In addition, if an insurance company wants to change the content of its claim form, it can do so independently of the other insurance companies, since the additional information is not transmitted via clearinghouse 600.

Beneficially, the simultaneous use of both clearinghouse and non-clearinghouse architectures reduces costs, allows for the direct digital interchange of data from one insurance company to another, and permits many different types of forms to be run off the same system, e.g. commercial insurance claims and workers' compensation claims can both be processed in the provider's office using the same customizable claim form. This produces a claims processing system which is more robust than anything on the market today.

During step S107, the PAC application is processed by the clearinghouse 600. Then, the insurance company accesses the PAC applications at the on-line service during step S108 and the PAC form of the PAC application at clearinghouse 600. In an exemplary case, each insurance company has an e-mail address specifically for the purpose of receiving the PAC applications. An insurance company accesses its e-mail box and finds a waiting list of PAC applications which are subsequently downloaded to GUI-capable computer system 310. In a preferred embodiment as shown in FIG. 3C, the GUI-capable computer system 310 is separate from the claims management mainframe computer 350 of the insurance company 300. Preferably, the GUI-capable buffer computer system 310 is a personal computer (PC) or a PC server which advantageously can be operated in parallel with but separate from the insurance company's mainframe computer 350.

In an exemplary case, this buffer computer 310 is part of a local area network (LAN) 313, which is connected by high bandwidth cables to personal computers or other GUI-capable terminals 311, 312 at the desks 360 and 370 of the individual reviewing dentists and claims adjusters, respectively. It should be noted that the necessary AIC software has been loaded onto the server 310 and onto the individual personal computers 311, 312. Preferably, once the patient's PAC application has been received, the system's AIC software at the insurance company's computer 310 automatically notifies the referring service provider that the PAC application has been received for processing, e.g., using a conventional e-mail message.

At step S109, the reviewing dentist calls up the PAC application, in an exemplary case, from both the server 310 to a personal computer 311 via the LAN 313 and the PAC form from the mainframe computer 350 to the terminal 351. See tasks T3 and T4 in FIG. 3C. It will be appreciated that all of the computers 310, 311 and 350 at insurance company 300 are, in the exemplary case, running AIC software. It should be noted that some small insurance companies may not even require server-LAN 310, 313 system discussed above, but just a single PC that will incorporate the functions of the elements 310, 311, 312, and 313. In any event, the reviewing dentist calls up a patient's PAC application on his personal computer 311 and terminal 351. When this happens, the system AIC software automatically inserts the insurance company's Predetermination Form into this file on, in an exemplary case, the buffer computer 310 (mainframe computer 350). The installed AIC software on buffer computer 310 (mainframe computer 350) advantageously can automatically transfer whatever information from the PAC form of the PAC application to the Predetermination form that is useful in completing the Predetermination form, e.g., repetitive information/fields. For instance, the service provider's Document Identification Number (PDIN) and the Provider Identification Number (PIN) can be transferred automatically to the Predetermination form. In addition, the AIC software can be written to display the information in the PAC form on the screen 311 (screen 351) in exactly the way that this particular insurance company wants it displayed.

With the AIC system described above, the use of "fields," the customizable claim form, and the placing of coordinated AIC software at both the service provider's office and the insurance company, has eliminated the problems associated with standardized forms. In short, the insurance company can elect to receive the PAC application, the digital attachment and desired field data, or the digital attachment alone from the computer 210 in the provider's office 200. The result is that each insurance company gets exactly the information it wants and has it displayed in exactly the way it wants. Thus, the compromise of a standardized claim form, as is required when using the NEIC system alone, is avoided.

In an exemplary case, the reviewing dentist is provided with two monitors on which can be displayed the three pages of the patient file. It will be appreciated that this configuration is optimized to facilitate rapid review of all parts of the PAC application. The reviewing dentist enters an Insurance Company Document Identification Number (DIN) at this point, which number is affixed to all three pages of the patient's file.

During step S110, the reviewing dentist reviews the PAC application. More specifically, the review process consists of a review of the medical facts or evidence (i.e., the text and x-ray information in digital attachment of the PAC application using computer 311), as well as a review of the patient's insurance policy on terminal 351. Once the reviewing dentist has made his analysis, he goes to the Predetermination form, i.e., the third page, and enters the required information to either approve or disapprove the procedure during step S111. The specific details regarding the information provided by the reviewing dentist will depend on the procedures established at each individual insurance company. Either the reviewing dentist or another person, e.g., a claims adjuster, will do the review of the patient's insurance policy. It will be appreciated that the benefits reviewer, i.e., either the reviewing dentist or the claims adjuster, need only select the patient's insurance ID number and his benefits sheet will be retrieved by the mainframe computer 350 for display on terminal 351. The benefits reviewer then reads off the information that must be entered in the Predetermination form and enters the information into, in an exemplary case, the computer system 310 (mainframe computer 350) using computer 311 (terminal 351) during step S111. It should again be noted that there is no electronic connection, in the preferred embodiment, between the mainframe computer 350 and the server 310. The reviewer can, at this time, also enter whatever additional information is deemed necessary by that particular insurance company into the mainframe computer 350. See task T5 in FIG. 3C.

Thus, in alternative exemplary cases, the Predetermination form advantageously can be completed by entering needed data into the mainframe 350 using the terminal 351 or it can be completed by entering needed data into the buffer computer 310 using the computer 311. Preferably, the completed Predetermination form is transmitted to the provider's office 200 either from the buffer computer 310 via the online service 400 or from the mainframe computer 350 using the clearinghouse 600, whichever is most convenient for the insurance company 300.

At this point, the Predetermination form is ready to be sent to the referring service provider. When the transmit icon on the computer screen of the benefit reviewer's computer 311 is activated, the following substeps are automatically performed:

(a) First, a check is performed to verify that the Predetermination form has been completely and properly filled out. If errors are detected, the AIC software notifies the operator via an appropriate annunciator;

(b) The Predetermination form and the patient's PAC application are downloaded to the buffer computer 310. See task T5 of FIG. 3C. From this platform, the company accesses the on-line service 400 and transmits the Predetermination form, i.e., just the information "fields," to the service provider's e-mail address, which is stored in the memory of server 310. See task T6 of FIG. 3C. In the AIC software, records are kept as to which PAC applications have been sent and when and to whom. The proper protocols are used so that when the application reaches the service provider, it arrives there as a computer readable file, i.e., the information is stored in "fields" that can be read by the AIC software at both the insurance company and the service provider's office;

(c) A hard copy of the Predetermination form and x-ray are printed, if desired, by the insurance company, see task T7 of FIG. 3C;

(d) The complete patient file is archived in the insurance company's computer system 310, 340, if desired. See task T8 of FIG. 3C. Otherwise, just the electronic Predetermination form and the PAC application are saved; and (e) The entire three page patient file is now cleared from the reviewing dentist's display 311 and the AIC software prompts the reviewing dentist as to whether another patient file should be accessed.

During step S112, the service provider accesses his e-mail address with the on-line service 400. All Predetermination forms which have been received are automatically delivered to the service provider's computer system 210 for insertion into the appropriate patient file. The service provider then reviews the Predetermination forms. Upon evaluating the decision of the reviewing dentist, the service provider can either perform the procedure (if approved) or discuss the matter with the patient's insurance company (if not approved).

During step S113, the approved procedure is performed by the service provider. Once the approved procedure has been completed, the service provider preferably sends in the Final Payment Claim (FPC) form. In an exemplary case, this could be as simple as just filling out another section of the Predetermination form and signing it using the electronic signature pen, as discussed above. It should be noted that in FIG. 3C, this is labeled as P*. Alternatively, if the insurance company so desires, a separate form just for this purpose can be employed. This latter form, which advantageously is stored in the memory of the provider's computer 210, must have the Insurance Company's DIN for this particular patient's procedure and all other needed information transferred to it, which advantageously can all be done by the AIC system software at step S114. At step S115, the Final Payment Claim form is transmitted back to the insurance company. See task T9 of FIG. 3C. In an exemplary case, activating the transmit icon on the service provider's computer system 210, e.g., by "clicking" on it, automatically results in the execution of the following substeps:

(a) A check is performed to see that the form has been completely and correctly filled out. If an error has occurred, the AIC software alerts the operator of the detected error;

(b) A hard copy of the form is printed out, if desired, by the service provider;

(c) The complete patient's electronic file is archived in the service provider's computer system 210, 240. It will be noted again that the patient's electronic file can be accessed by patient name, social security number, document identification number, etc.; and (d) The computer system 210 establishes a connection with the clearinghouse 600 and transmits the patient's Final Payment Claim (FPC) form to the insurance company's e-mail address.

As previously discussed, the AIC software on the service provider's computer system 210 advantageously may include facilities for transmitting the Final Payment Claim form to the insurance company at a later time, e.g., for transmitting all of the days PAC application and FPC forms at one time.

It will also be noted, as discussed above, that the AIC software maintains records as to which claim form was sent and when it was sent to the insurance company. In an exemplary case, the e-mail address to which the Final Payment Claim form is sent is different from the address used in transmitting the PAC application. Since the Final Payment Claim form does not include a digitized image, i.e., a digitized x-ray, the insurance company may choose to have the Final Payment Claim form directed to an e-mail address accessible from the mainframe computer 350.

The insurance company then receives the Final Payment Claim forms during step S116 when it accesses its Final Payment Claim forms mail box. In an exemplary case, the computer system receiving the Final Payment Claim forms is the claims management mainframe computer 350 of the insurance company 300. The Final Payment Claim form is retrieved from mainframe computer 350 using the terminal 352 located at the claims adjusters' desk. See task T10 of FIG. 3C. Alternatively, the Final Payment Claim form advantageously can be retrieved from buffer computer 310 using the computer 312 located at the claims adjusters' desk when the Final Payment Claim form is addressed to the buffer computer, i.e., server, 310. It should again be noted that the appropriate AIC software modules have been loaded onto the server 310, the personal computer 312 and the mainframe computer 350.

The Final Payment Claim form is then reviewed during step S117. The adjuster reviewing the Final Payment Claim form can, if necessary, call up the PAC application from the memory of the server 310, since the original Insurance Company Document Identification Number for the corresponding PAC application was transferred to the Predetermination form and, thus, to the Final Payment Claim form. In addition, the adjuster can, if need be, call up the information on the insurance policy of the particular patient. Preferably, the insurance company 300 provides the adjuster with a separate monitor 352 connected to the claims management software on mainframe computer 350.

Whatever internal paperwork is necessary to be filled out is automatically downloaded with the Final Payment Claim form itself by the appropriate AIC software module. Part of this paperwork will preferably be form(s) which must be completed so as to order a check issued to the service provider along with an Explanation of Benefits (EOB). Also at step S118, whatever information is necessary to be entered into the mainframe can be done through the use of the terminal 352.

Finally, upon activating the transmit icon on the insurance company's personal computer 312 (terminal 352), the following substeps are automatically executed:

(a) A check is again preformed to see that the form has been completely and correctly completed and the operator is notified if an error has occurred;

(b) A hard copy of the form is printed out, if desired by the insurance company;

(c) The complete patient file is archived in the insurance company's computer system, e.g., on the server. It should again be noted that the patient file can be accessed using the patient's name, social security number, or an assigned document identification number, etc.; and (d) A payment draft is issued, in the approved amount, to the service provider. This can be done through any number of methods, including printing a hard copy check and forwarding it through the U.S. postal service, electronic funds transfer, etc. Each form of payment will be accompanied with the normal description of the service to which these funds should be applied, i.e., the EOB (Explanation of Benefits).

The preferred embodiments of FIGS. 3A-3C were described as transmitting digitized dental x-rays as part of an integrated PAC application file transmitted between a service provider and an insurance company. However, the present invention is broadly directed to the integrated transmission of any "electronic text form" and any "attachment." Further, the present invention is not limited to transmissions between providers and insurance companies. Rather, it is intended to facilitate the transmission of electronic forms with attachments between any person or organization and any other person or organization.

For example, the present invention has utility in such other areas as Property/Casualty Insurance and law enforcement. Thus, the "attachment" need not be an x-ray or other type of image. Rather it can be any information which is not easily incorporated into an associated "electronic text form" and/or cannot be easily displayed on an existing legacy computer system. Attachments can include, but are not limited to, pictures, graphs, sound recordings, and nonstandard text. Examples would be x-rays, CTs, MRIs, EKG or EEG recordings, i.e., strip charts, digitized video signals such as Moving Picture Experts Group (MPEG) compressed video signals, transcriptions of Operating Room Notes, estimates for repairs to a house or car, EOBs (Explanation of Benefits), additional ASCII text, and the like. As used in this description, all particulars regarding a specific "attachment," such as medical specialty, acquiring modality, the patient's problem, etc., can be ignored. These are details having absolutely no bearing on the essence of the present invention. The only requirements are that the information must be something that can be digitized and therefore put into the form of a computer file, and that once in this form, it can be "read, reviewed or interpreted" by the person or organization receiving it.

The exemplary preferred embodiment as depicted in FIG. 3A and discussed above address only a stand-alone system of computers, which is independent of the practice management software in the local dentist's office, the claims management software at each insurance company, and of clearinghouses such as NEIC. However, from the embodiments as depicted in FIGS. 3B and 3C, it will be appreciated that there is an entire spectrum of different ways to structure a system which will support "attachment integrated claims" which will be readily apparent to a person of ordinary skill in the art (after having the benefit of the present disclosure), all of which are encompassed by the present invention.

It should also be noted that the AIC software described thus far has been independent of the service provider's practice management software. However, one alternative preferred embodiment calls for integrating the AIC software with the practice management software. This would further reduce the amount of time spent actually filling out the PAC application and the other paperwork involved in the overall claims process.

Electronic filing of standard 100% text claims is now being supported by many practice management systems and by stand-alone electronic claims software systems. In another alternative preferred embodiment, the AIC software could be incorporated into these systems as a means of sending the x-ray part of the PAC application.

It should also be mentioned that the present invention represents a total solution on three levels to the problem of streamlining the processing of insurance claim forms with attachments. First, the system from provider to third party payer is totally digital. The present invention includes an integrated system of hardware and AIC software that allows: (1) providers to create an electronic (digital) version of a patient's PAC application (text and x-ray); (2) providers to transmit the PAC application to an insurance company; and (3) the insurance company to read the patient's PAC application. Thus, it creates a coherent system for the filing, transmission and processing of "claims with attachments."

Secondly, the present invention is an industry-wide system which allows every provider to interface with every third party payer. Finally, the present invention is a system which permits all communications between the service provider and the insurance company to be totally electronic. The present invention makes the entire process electronic from the initial preparation of the PAC form to the payment of the final claim. Communication is digital in both directions.

As discussed above with reference to FIGS. 3A-3B, the patient, the service provider, the insurance company, or any combination thereof may prefer that all communication be performed through a value-added service provider 500. Also, it should be mentioned that for the embodiment depicted in FIG. 3C, since the PAC application, i.e., PAC form and digital attachment, can be transmitted to the insurance company 300 using an online service while only the PAC form is transmitted to the insurance company 300 using the clearinghouse 600, the patient, the service provider, the insurance company, or any combination thereof may prefer that all communication be performed through a value added service provider (not shown in FIG. 3C) connected to the online service 400. The services performed by the value added service provider in each of the embodiments described with reference to FIGS. 3A-3C advantageously could include any or all of the services listed immediately below.

First, the value-added service provider 500 may act as a National Dental Data Bank (NDDB), i.e., a data bank storing patient dental images. Limited information regarding the patient from the PAC form is attached to the digital x-ray to produce a digitized x-ray record. This information could include, for example, the date that the x-ray was taken, the identity of the service provider who took the x-ray, the patient's name and social security number, etc. The digitized x-ray record is archived at NDDB for the patient. This would allow the retrieval of the x-ray by the patient at any time for any reason, e.g., the patient could ask that the x-ray and claim be sent to another dentist for a second opinion and/or for a second price estimate. In fact, the patient may request that the PAC application be sent to other qualified service providers so that they could competitively bid on the needed procedure.

In addition to the NDDB function, the value-added service provider 500 could perform prescreening of the PAC applications for errors and could provide statistics to both the service providers and the insurance companies regarding, for example, the frequency at which a procedure is performed or the frequency at which follow up treatment is required after a first procedure is performed. The value-added service provider 500 could also do the prior approval review for an insurance company or could provide other services tailored to suit the needs of the service provider, the patient, and/or the individual insurance company.

It should be mentioned that there are three outside areas of software that advantageously can be taken into consideration, or ignored, with the present invention. These are practice management software run by the service provider, claims management software run by the insurance company, and clearinghouse software. The present invention allows for the entire spectrum of interfacing, from a totally stand-alone system for electronic claims processing to one that is fully integrated with practice management software, claims management software, and the NEIC. Moreover, the present invention is specifically contrived so that it can be used simultaneously in all modes. That is, one insurance company could choose to have no interfacing between the computer 310 running the AIC software and its mainframe computer 350, while, at the same time, another insurance company could choose to have AIC software running simultaneously on both the mainframe computer 350 and the buffer computer system 310. Thus, each operating mode or methodology could be considered to be a different preferred embodiment of the present invention, notwithstanding the fact that all modes are expected to be operating simultaneously.

The present invention was motivated by a desire to solve a problem which has existed for many years. The AIC software was designed with this in mind. Thus, for example, redundant information is automatically moved from one form and file to another along the chain of operating steps, i.e., from one document to another within a given insurance company's set of forms. Moreover, the AIC software advantageously can be written in C++ or some other appropriate programming language. The reason for this is so that when information in entered into areas of the electronic PAC forms, it is entered as a "field." Being a "field" it can be used as a logic control device, as discussed in greater detail above.

The overall workflow problem to be addressed is treated as a coherent whole. Thus, AIC software is specifically designed so that, at each step of the preferred operating method, the fact that the information is in digital form is used to streamline the process. Thus, the AIC software is designed to eliminate inefficiencies and deficiencies that exist in current claims handling systems. For example, the information itself can be used as a logical control device and it can also be transferred from one document to another. It should be noted that all available forms are written into the AIC software so that they are coordinated with one another, that is, they know where each has a similar "field."

It should also be noted that the AIC software automates much of the overall insurance claims processing, thus eliminating many of the areas that are repetitive or prone to human error. These areas include the following:

(a) Filling in the service provider's information. Although each insurance company may require something different in the way of service provider information, the AIC software can store consolidated service provider information so that the information need be entered only once. For example, the service provider need only enter his telephone number once; the AIC software can reformat this basic information specifically for each individual insurance company's form;

(b) Transmitting the PAC application to the correct e-mail address, thus eliminating the errors associated with hand addressing and stamping the mailing envelope;

(c) Checking each completed form, i.e., PAC application and Predetermination form, for accuracy and completeness, while it is still at the provider's office or the insurance company; and (d) Simultaneously transmitting, archiving, and printing the completed forms, e.g., the PAC application.

It will be appreciated that many such advantages will be evident to those of ordinary skill in the art from having the requisite PAC form stored in the AIC software on the service provider's computer system 210, 240.

Moreover, the AIC system advantageously can be optimized to limit unnecessary information. For example, the system can make use of scanners 220 which have portions of their scanning area physically or electronically masked out, which reduces both scanning time and transmission time by minimizing the size of the digitized x-ray produced, for example, during step S104. The provisions for the use of digital and digitized signatures also eliminates unneeded paper shuffling.

It should again be noted that the major improvement in efficiency attributable to the AIC system results from combining or coordinating an electronic PAC form with an electronic (digitized) x-ray. This electronic x-ray will have a document identification number assigned to it.

In addition, the AIC system and corresponding method according to preferred embodiments of the present invention provide several convenience features which are only possible when using a fully electronic filing system. For example, the AIC system facilitates automatic acknowledgment by the insurance company that it has received the PAC application. Moreover, the AIC system provides automatic transfer of pertinent information from the PAC application to the Predetermination form. Furthermore, the AIC system components at the insurance company preferably allow simultaneous viewing of the three documents needed to complete the Predetermination form. In addition, the AIC system and requisite software automates the entire transmitting and archiving processes of the PAC application and the Predetermination form at the insurance company.

In some instances, the electronic reuse of the Predetermination form as the Final Payment Claim form means that the service provider need only indicate the date that the procedure was performed and enter the service provider's facsimile or electronic signature. The AIC software module at the provider's office requests these be entered into P, i.e., the Predetermination form, to create P*, i.e., the Final Payment Claim form, and then transmits P* to the final claims e-mail address for payment. Moreover, the only information that needs to be sent from the service provider to the insurance company is the insurance company's assigned document identification number, the date of completion and the service provider's signature.

The preferred embodiments of the AIC system according to the present invention provide dentists in the field with the necessary hardware and software which allows them to create an electronic (digital) version of a patient's PAC application, both the text and the required patient x-ray. The AIC software automatically adds these two data types together to form a single entity, the patient's PAC application. Moreover, the AIC system provides the insurance companies with hardware and software which allows them to read the patient's electronic PAC application. For each insurance company, this application is tailored so that it contains the specific information required by that company and it contains that information in the form required by that company. As such, the necessity to force standard formats on the insurance industry is eliminated. Moreover, the AIC system and software automatically attaches a partially filled out Predetermination form to the patient's PAC application when it is called up for review and approval. Moreover, the AIC system and software completely eliminates the time consuming process of actually handling the patient's film x-ray by insurance company personnel.

Other modifications to and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention, as defined in the appended claims.

What is claimed is:

1. A computer implemented method, for processing insurance transactions that require attachments, the method comprising the steps of:

receiving digital data at a first computer,
wherein the digital data comprises a first computer file and a second computer file, both of which contain information about a particular insurance encounter;
wherein at least some of the digital data in the first computer file and at least some of the digital data in the second computer file are in a first set of identifiable data fields;
wherein the first computer file and the second computer file are cross-referenced with each other;
wherein the first computer file contains at least attachment data and the second computer file contains at least insurance transaction data;
wherein at least some of the insurance transaction data and the attachment data comprise digital data in the first set of identifiable data fields;

examining via the first computer the identifiable fields of the digital data to determine which fields contain insurance transaction data and which fields contain attachment data;

storing first digital data in the first computer, wherein the first digital data comprises at least some of the attachment data;

transmitting second digital data from the first computer to a second computer, wherein the second digital data comprises at least some of the insurance transaction data;

storing the second digital data in the second computer,
wherein the insurance transaction data stored in the second computer and the attachment data stored in the first computer are cross-referenced with each other;
wherein at least some of the data included in the first digital data is excluded from the second digital data; and processing an insurance transaction by entering data into at least one identifiable field in a second set of identifiable data fields using at least some of the data in the first set of identifiable data fields in a logic process to determine the data to be entered into the at least one identifiable field in the second set of identifiable data fields.

2. The method of claim 1, wherein the excluded data comprises at least some of the attachment data.

3. The method of claim 1, wherein the processing step comprises displaying at least some of said insurance transaction data and said attachment data on at least one computer display device.

4. The method of claim 1, wherein the processing step comprises inputting data into a form using a data inputting device.

5. The method of claim 4, wherein the inputting device comprises a keyboard.

6. The method of claim 4, wherein the form is selected from the group consisting of an explanation of benefits form, a payment form, and a predetermination form.

7. The method of claim 1, wherein the at least some of the insurance transaction data transmitted from the first computer to the second computer is data in a subset of the first set of identifiable data fields.

8. The method of claim 7, wherein the subset of the first set of identifiable data fields is specified using the identities of the fields.

9. The method of claim 1, wherein the processing step comprises using data from at least one of the identifiable data fields in the first set of identifiable data fields to complete at least one identifiable field in an electronic form.

10. The method of claim 9, wherein the form is selected from the group consisting of an explanation of benefits form, a payment form, and a predetermination form.

11. The method of claim 9, wherein the method further comprises the step of transmitting said form to a computer operated for a provider.

12. The method of claim 11, wherein the provider is a healthcare provider.

13. The method of claim 9, wherein the method further comprises the step of archiving said form as a computer file.

14. The method of claim 9, wherein the method further comprises the step of storing at least some of the data in said form in identifiable data fields.

15. The method of claim 1, wherein the entering step comprises completing at least one identifiable data field in an explanation of benefits statement, a payment statement, a predetermination statement, or a database.

16. The method of claim 1, wherein the method further comprises the step of transmitting at least some of the completed second set of identifiable data fields to a computer operated for a provider.

17. The method of claim 16, wherein the provider is a healthcare provider.

18. The method of claim 1, wherein the method further comprises the step of accessing at least one of the first and the second digital data using the cross-referencing data.

19. The method of claim 1, wherein the first digital data comprises data in a first set of $N_1$ identifiable data fields, and the second digital data comprises data in a second set of $N_2$ identifiable data fields.

20. The method of claim 1, wherein the receiving step comprises receiving a computer file comprising the digital data.

21. The method of claim 1, wherein the receiving step comprises the steps of:
receiving the first computer file comprising at least some of the attachment data, and
receiving the second computer file comprising at least some of the insurance transaction data,
wherein at least some of the data included in the first computer file is excluded from the second computer file.

22. The method of claim 21, wherein the excluded data comprises at least some attachment data.

23. The method of claim 1, wherein the method further comprises the step of archiving at least some of the digital data as a computer file.

24. The method of claim 1, wherein the method further comprises the step of storing at least some of the digital data in identifiable data fields.

25. The method of claim 1, wherein the received digital data comprises cross-referencing data for associating the insurance transaction data with the attachment data.

26. The method of claim 1, wherein the method further comprises the step of cross-referencing the insurance transaction data and the attachment data.

27. The method of claim 1, wherein the cross-referencing data comprises at least one identification number.

28. The method of claim 1, wherein the cross-referencing data comprises at least one selected from the group consisting of at least one identification number, at least some of the insurance transaction data, healthcare provider document identification data, insurance payer document identification data, healthcare payer document identification data, healthcare transaction identification data, identification number, healthcare-insurance-claim attachment identification number, and data that identifies a healthcare encounter.

29. The method of claim 1, wherein the computer system is operated for an insurance payer.

30. The method of claim 29, wherein the insurance payer is selected from the group consisting of a dental insurance payer, a medical insurance payer, a healthcare insurance payer, a property insurance payer, a worker's compensation insurance payer, and casualty insurance payer.

31. The method of claim 30, wherein the first computer comprises a buffer computer system and the second computer comprises a legacy computer system.

32. The method of claim 31, wherein the legacy computer system is a health-insurance-claims management computer system.

33. The method of claim 32, wherein the attachment data is health-insurance-claims attachment data and the insurance transaction data is health-insurance-claims data.

34. The method of claim 31, wherein said buffer computer system is configured by software for displaying at least some of said attachment data on a computer display device.

35. The method of claim 1, wherein the receiving step comprises receiving the digital data from a computer system operated for at least one selected from the group consisting of a value added service, a provider, an insurance provider, a healthcare provider, and a clearinghouse.

36. The method of claim 1, wherein the insurance transaction data comprises information selected from the group consisting of dental data, medical data, healthcare data, worker's compensation data, property and casualty insurance transaction information.

37. The method of claim 1, wherein the insurance transaction data comprises at least one selected from the group consisting of an identification number, transaction identification data, beneficiary information, beneficiary name, patient data, patient name, healthcare provider data, healthcare provider name, healthcare provider identification data, healthcare provider document identification data, healthcare payer identification data, healthcare payer name, healthcare payer identification number, healthcare payer document identification data, healthcare-insurance-claim attachment identification number, description of service provided, date of service, healthcare encounter information, prior approval claim data, and worker's compensation data.

38. The method of claim 1, wherein the attachment data comprises an attachment selected from a group consisting of a picture, a graph, a sound recording, nonstandard text, a digitized x-ray, an explanation of benefits, a CT, an MRI, a EKG, a EEG, a strip chart, a digitized video signals, a transcription of operating room notes, supplemental data to a health insurance claims, and additional ASCII text.

39. The method of claim 1, wherein the transmitting step includes transmitting the cross-referencing data from the first computer to the second computer.

40. The method of claim 1, wherein the second data comprises only a portion of the at least some of the insurance transaction data transmitted from the first computer to the second computer.

41. A computer system configured to process insurance transactions that require attachments, the computer system comprising:
   first and second computers;
   memory; and
   software in the memory configured to cause the computer system to:
      receive digital data at the first computer,
         wherein the digital data comprises a first computer file and a second computer file, both of which contain information about a particular insurance encounter;
         wherein at least some of the digital data in the first computer file and at least some of the digital data in the second computer file are in a first set of identifiable data fields;
         wherein the first computer file and the second computer file are cross-referenced with each other;
         wherein the first computer file contains at least attachment data and the second computer file contains at least insurance transaction data;
         wherein at least some of the insurance transaction data and the attachment data comprise digital data in the first set of identifiable data fields;
      examine via the computer system the identifiable fields of the digital data to determine which fields contain insurance transaction data and which fields contain attachment data;
      store first digital data in the first computer, wherein the first digital data comprises at least some of the attachment data;
      transmit second digital data from the first computer to the second computer, wherein the second digital data comprises at least some of the insurance transaction data;
      store the second digital data in the second computer;
         wherein the insurance transaction data stored in the second computer and the attachment data stored in the first computer are cross-referenced with each other;
         wherein at least some of the data included in the first digital data is excluded from the second digital data; and
      process an insurance transaction by entering data into at least one identifiable field in a second set of identifiable data fields using at least some of the data in the first set of identifiable data fields in a logic process to determine the data to be entered into the at least one identifiable field in the second set of identifiable data fields.

42. The computer system of claim 41, wherein the excluded data comprises at least some of the attachment data.

43. The computer system of claim 41, wherein the processing of the insurance transaction comprises displaying at least some of said insurance transaction data and said attachment data on at least one computer display device of the computer system.

44. The computer system of claim 41, wherein the processing of the insurance transaction comprises inputting data into a form using a data inputting device.

45. The computer system of claim 44, wherein the data inputting device comprises a keyboard.

46. The computer system of claim 44, wherein the form is selected from the group consisting of an explanation of benefits form, a payment form, and a predetermination form.

47. The computer system of claim 41, wherein the at least some of the insurance transaction data transmitted from the first computer to the second computer is data in a subset of the first set of identifiable data fields.

48. The computer system of claim 47, wherein the subset of the first set of identifiable data fields is specified using the identities of the fields.

49. The computer system of claim 41, wherein the processing of the insurance transaction comprises the computer system using data from at least one of the identifiable data fields in the first set of identifiable data fields to complete at least one identifiable field in an electronic form.

50. The computer system of claim 49, wherein the form is selected from the group consisting of an explanation of benefits form, a payment form, and a predetermination form.

51. The computer system of claim 49, wherein the software further adapts the computer system to transmit said form to a computer operated for a provider.

52. The computer system of claim 51 wherein the provider is a healthcare provider.

53. The computer system of claim 49, wherein the software further causes the computer system to archive said form as a computer file.

54. The computer system of claim 49, wherein the software further causes the computer system to store at least some of the data in said form in identifiable fields.

55. The computer system of claim 41, wherein the at least one identifiable field in the second set of identifiable fields comprises an explanation of benefits statement, a payment statement, a predetermination statement, or a database.

56. The computer system of claim 41, wherein the software further adapts the computer system to transmit at least some of said second set of completed identifiable fields to a computer operated for a provider.

57. The computer system of claim 56, wherein the provider is a healthcare provider.

58. The computer system of claim 41, wherein the software further adapts the computer system to access at least one of the first and the second digital data using the cross-referencing data.

59. The computer system of claim 41, wherein the first digital data comprises data in a first set of $N_1$ identifiable data fields, and the second digital data comprises data in a second set of $N_2$ identifiable data fields.

60. The computer system of claim 41, wherein the digital data comprises a computer file.

61. The computer system of claim 41, wherein at least some of the data included in the first computer file is excluded from the second computer file.

62. The computer system of claim 61, wherein the excluded data comprises at least some attachment data.

63. The computer system of claim 41, wherein the software further causes the computer system to archive at least some of the digital data as a computer file.

64. The computer system of claim 41, wherein the software further causes the computer system to store at least some of the digital data in identifiable fields.

65. The computer system of claim 41, wherein the received digital data comprises cross-referencing data for associating the insurance transaction data with the attachment data.

66. The computer system of claim 41, wherein the software further adapts the computer system to cross-reference the insurance transaction data and the attachment data.

67. The computer system of claim 41, wherein the cross-referencing data comprises at least one identification number.

68. The computer system of claim 41, wherein the cross-referencing data comprises at least one selected from the group consisting of at least one identification number, at least some of the insurance transaction data, healthcare provider document identification data, insurance payer document identification data, healthcare payer document identification data, healthcare transaction identification data, identification number, healthcare-insurance-claim attachment identification number, and data that identifies a healthcare encounter.

69. The computer system of claim 41, wherein the computer system is operated for an insurance payer.

70. The computer system of claim 69, wherein the insurance payer is selected from the group consisting of dental insurance payer, medical insurance payer, healthcare insurance payer, property insurance payer, worker's compensation insurance payer, and casualty insurance payer.

71. The computer system of claim 69, wherein the first computer comprises a buffer computer system and the second computer comprises a legacy computer system.

72. The computer system of claim 71, wherein the legacy computer system is a health-insurance-claims management computer system.

73. The computer system of claim 71, wherein the attachment data is health-insurance-claims attachment data and the insurance transaction data is health-insurance-claims data.

74. The computer system of claim 71, wherein the buffer computer system is configured by software to display at least some of said attachment data on a computer display device.

75. The computer system of claim 41, wherein the digital data is receive from a computer system operated for at least one selected from the group consisting of a value added service, a provider, an insurance provider, a healthcare provider, and a clearinghouse.

76. The computer system of claim 41, wherein the insurance transaction data comprises information selected from the group consisting of dental data, medical data, healthcare data, worker's compensation data, property insurance transaction data, and casualty insurance transaction information.

77. The computer system of claim 41, wherein the insurance transaction data comprises at least one selected from the group consisting of identification number, transaction identification data, beneficiary information, beneficiary name, patient data, patient name, healthcare provider data, healthcare provider name, healthcare provider identification data, healthcare provider document identification data, healthcare payer identification data, healthcare payer name, healthcare payer identification number, healthcare payer document identification data, healthcare-insurance-claim attachment identification number, description of service provided, date of service, healthcare encounter information, prior approval claim data, and worker's compensation data.

78. The computer system of claim 41, wherein the attachment data comprises an attachment selected from a group consisting of a picture, a graph, a sound recording, nonstandard text, a digitized x-ray, an explanation of benefits, a CT, an MRI, a EKG, a EEG, a strip chart, a digitized video signals, a transcription of operating room notes, supplemental data to a health insurance claim, and additional ASCII text.

79. The computer system of claim 41, wherein the software further adapts the computer system to transmit the cross-referencing data from the first computer to the second computer.

80. The computer system of claim 41, wherein the second data comprises only a portion of the at least some of the insurance transaction data transmitted from the first computer to the second computer.

81. A computer implemented method, for processing electronic communications, the method comprises the steps of:
receiving, from a source external to a computer system, an electronic communication comprising first digital data in $N_1$ identifiable data fields, wherein $N_1$ is an integer and wherein at least some of the $N_1$ identifiable data fields comprise insurance transaction data and at least one of the $N_1$ identifiable data fields comprises attachment data for at least one attachment stored in memory of a first computer;
storing the electronic communication in memory of a second computer;
processing the electronic communication by:
displaying at least one graphic user interface screen comprising a set of $N_2$ identifiable data fields, wherein $N_2$ is an integer, and the attachment; and
determining second digital data to be entered in at least one field in the set of $N_2$ identifiable data fields using at least some of the insurance transaction data in the set of $N_1$ identifiable data fields in a logic process;
wherein the second digital data comprises insurance transaction data and wherein the second digital data excludes the attachment.

82. The method of claim 81, wherein the attachment data comprises the attachment.

83. The method of claim 81, wherein the first digital data comprises patient healthcare data and is received from a healthcare provider.

84. The method of claim 81, wherein the first digital data comprises at least patient identification data and physician identification data.

85. The method of claim 81, further comprising the step of receiving additional digital data into at least one field in the graphic user interface.

86. The method of claim 81, further comprising the step of copying the first digital data from at least one field in the $N_1$ identifiable data fields into at least one field of the $N_2$ second identifiable data fields.

87. The method of claim 81, further comprising the step of printing at least some of the second digital data.

88. The method of claim 81, wherein the method further comprises the step of transmitting at least some of the second digital data.

89. A method, implemented by a server computer, for processing electronic communications, the computer system comprising memory and at least one display device, the method comprises the steps of:

receiving, from a source external to the computer system, an electronic communication comprising digital data in N identifiable data fields, wherein N is an integer;

displaying at least a first and a second graphic user interface screen, wherein said first graphic user interface screen comprises a first set of $N_1$ identifiable data fields, wherein $N_1$ is an integer, wherein said second graphic user interface screen comprises a second set of $N_2$ identifiable data fields, and wherein $N_2$ is an integer;

copying first digital data from at least a first field of the N identifiable fields into at least one of the $N_1$ identifiable fields;

copying second digital data from at least a second field of the N identifiable data fields into at least one of the $N_2$ identifiable data fields;

wherein digital data copied into the at least one of the $N_2$ identifiable fields of the second graphic user interface screen excludes at least some of the digital data copied into the at least one of the $N_1$ identifiable fields of the first graphic user interface screen; and determining the digital data to be displayed in at least one identifiable data field in the sets of $N_1$ and $N_2$ identifiable data fields using at least some of the digital data in the set of N identifiable data fields in a logic process.

90. The method of claim 89, wherein the digital data comprises healthcare data of a patient.

91. The method of claim 89, wherein the digital data is received from a healthcare provider.

92. The method of claim 89, wherein the digital data comprises at least patient identification data and physician identification data.

93. The method of claim 89, further comprising the step of receiving additional digital data into at least one field of the set of $N_1$ identifiable data fields or the set of $N_2$ identifiable data fields from a keyboard or a mouse.

94. The method of claim 89, further comprising the step of printing at least some of the data in the sets of $N_1$ and $N_2$ identifiable data fields.

95. The method of claim 89, wherein the method further comprises the step of transmitting at least some of the data in the sets of $N_1$ and N2 identifiable data fields.

96. The method of claim 1, further comprising:
wherein the attachment data comprises at least one selected from a group consisting of a picture, a graph, a sound recording, a digitized x-ray, a CT, an MRI, a EKG, a EEG, a strip chart, an EOB, and a digitized video signal; and
wherein the insurance transaction data comprises alphanumeric data and does not comprise a picture, a graph, a sound recording, a digitized x-ray, a CT, an MRI, a EKG, a EEG, a strip chart, an EOB, or a digitized video signal.

97. The method of claim 1, wherein the attachment data comprises image data, and wherein the insurance transaction data comprises alphanumeric data and does not comprise image data.

98. The method of claim 1, further comprising:
wherein the second computer file comprises a request for payment by a medical provider; and
wherein the first computer file comprises medical evidence supporting the request for payment.

99. The method of claim 1, further comprising:
wherein the second computer file comprises a request for payment by a medical provider; and
wherein the first computer file comprises medical evidence supporting the request for payment, and wherein the medical evidence is selected in response to a medical procedure being claimed for payment in the second computer file.

100. The method of claim 1, further comprising:
wherein the attachment data which is in identifiable fields comprises at least one selected from a group consisting of a picture, a graph, a sound recording, a digitized x-ray, a CT, an MRI, a EKG, a EEG, a strip chart, an EOB, and a digitized video signal; and
wherein the insurance transaction data which is in identifiable fields consists of alphanumeric data.

* * * * *

UNITED STATES PATENT AND TRADEMARK OFFICE
CERTIFICATE OF CORRECTION

| | | |
|---|---|---|
| PATENT NO. | : 8,676,609 B2 | Page 1 of 1 |
| APPLICATION NO. | : 11/653104 | |
| DATED | : March 18, 2014 | |
| INVENTOR(S) | : Andrew L. DiRienzo | |

It is certified that error appears in the above-identified patent and that said Letters Patent is hereby corrected as shown below:

On the Title Page, item (73), the Assignee name, replace "Systens" with --Systems--

Signed and Sealed this
Twelfth Day of August, 2014

Michelle K. Lee
*Deputy Director of the United States Patent and Trademark Office*